United States Patent [19]

Wertz et al.

[11] 4,448,534
[45] May 15, 1984

[54] ANTIBIOTIC SUSCEPTIBILITY TESTING

[75] Inventors: Richard K. Wertz; Albert M. Cook; James C. Hathaway, all of Sacramento, Calif.

[73] Assignee: American Hospital Corporation, Evanston, Ill.

[21] Appl. No.: 82,228

[22] Filed: Oct. 5, 1979

Related U.S. Application Data

[63] Continuation-in-part of Ser. No. 891,648, Mar. 30, 1978, abandoned.

[51] Int. Cl.³ .............................................. G01J 3/46
[52] U.S. Cl. .................................... 356/435; 356/436; 356/442
[58] Field of Search ............... 356/432, 433, 434, 435, 356/436, 441, 442

[56] References Cited

U.S. PATENT DOCUMENTS

| | | |
|---|---|---|
| Re. 28,800 | 9/1974 | Acker et al. . |
| Re. 28,801 | 9/1974 | Acker et al. . |
| 3,325,594 | 6/1967 | Goldhammer et al. . |
| 3,504,981 | 4/1970 | Malvin . |
| 3,533,744 | 10/1970 | Unger . |
| 3,627,431 | 12/1971 | Komarniski ......................... 356/441 |
| 3,656,856 | 4/1972 | Katz et al. . |
| 3,697,185 | 10/1972 | Kassel et al. . |
| 3,703,336 | 11/1972 | Rosse et al. . |
| 3,723,062 | 3/1973 | Dahms . |
| 3,734,621 | 5/1973 | Moody et al. . |
| 3,763,374 | 10/1973 | Tiffany et al. . |
| 3,773,426 | 11/1973 | Mudd .................................. 356/435 |
| 3,810,696 | 5/1974 | Hutchins ............................. 356/434 |
| 3,817,632 | 6/1974 | Picunko et al. . |
| 3,829,218 | 8/1974 | Alyanak ............................. 356/300 |
| 3,832,532 | 8/1974 | Praglin et al. . |
| 3,847,486 | 11/1974 | McCabe . |
| 3,873,273 | 3/1975 | Moran et al. . |
| 3,969,079 | 7/1976 | Catarious et al. . |
| 3,970,393 | 7/1976 | Krygeris et al. ..................... 356/435 |
| 4,004,150 | 1/1977 | Natelson . |
| 4,055,752 | 10/1977 | Kappe et al. . |
| 4,063,816 | 12/1977 | Itol et al. . |
| 4,063,817 | 12/1977 | Shimamura et al. . |
| 4,080,075 | 3/1978 | Berg . |
| 4,125,828 | 11/1978 | Resnick et al. ................. 250/461 B |
| 4,128,339 | 12/1978 | Yamazaki et al. . |
| 4,144,030 | 3/1979 | Suovaniemi ......................... 356/435 |

Primary Examiner—R. A. Rosenberger
Attorney, Agent, or Firm—Owen, Wickersham & Erickson

[57] ABSTRACT

Apparatus is provided for automatically scanning electronically each well of a multi-well tray containing many liquid samples. A light source, preferably a single source, is passed through the wells to an array of photosensitive cells, one for each well. There is also a calibrating or comparison cell receiving the light. Electronic apparatus reads each cell in sequence, quickly completing the scan without physical movement of any parts. The resultant signals are compared with the signal from the comparison cell and with other signals or stored data and determinations are made and displayed or printed out. Thereby, and by the methods of the invention, such matters as minimum inhibitory concentrations (MIC) of drugs and identification of microorganisms are achieved.

17 Claims, 21 Drawing Figures

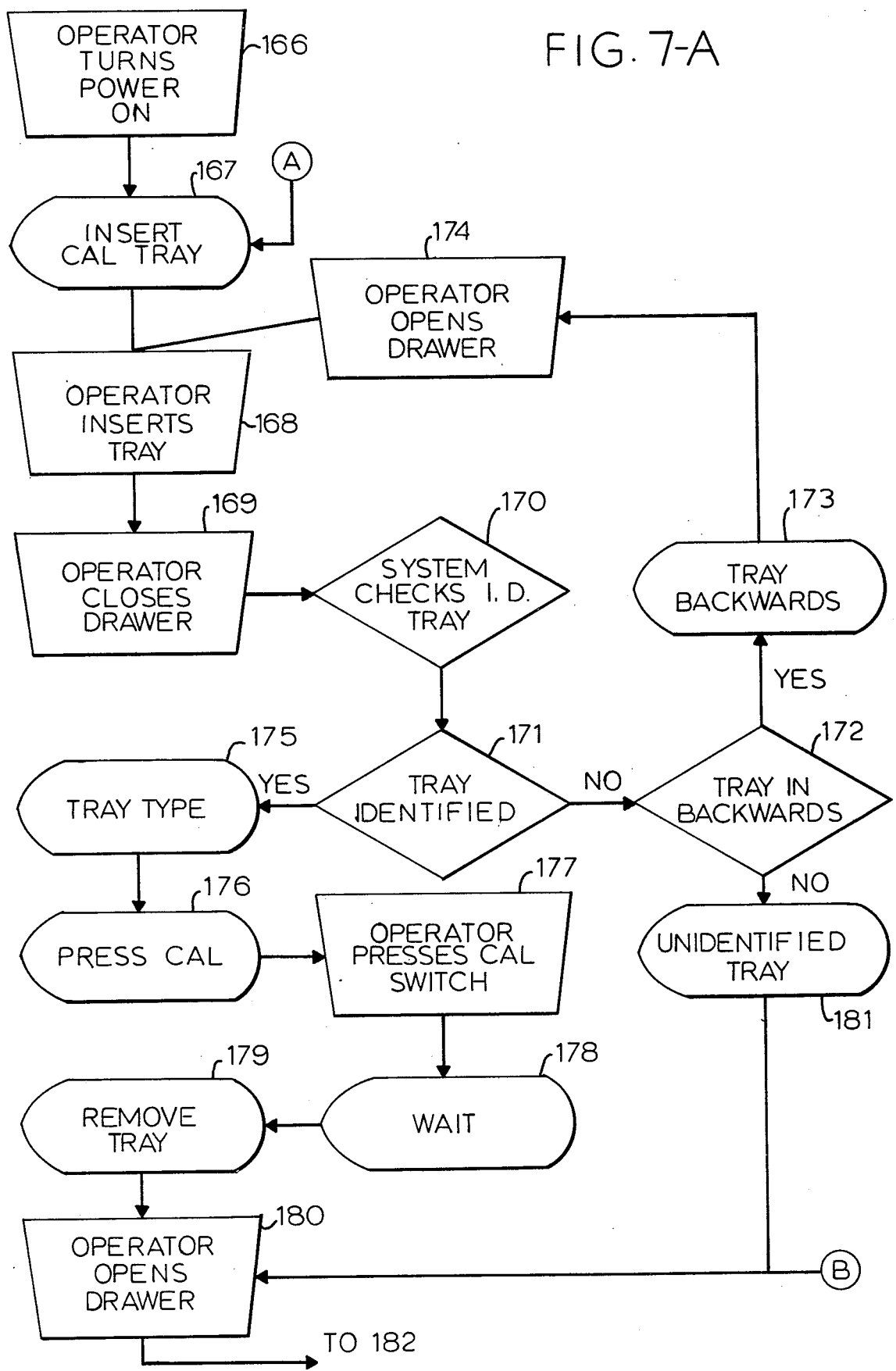
FIG. 7-A

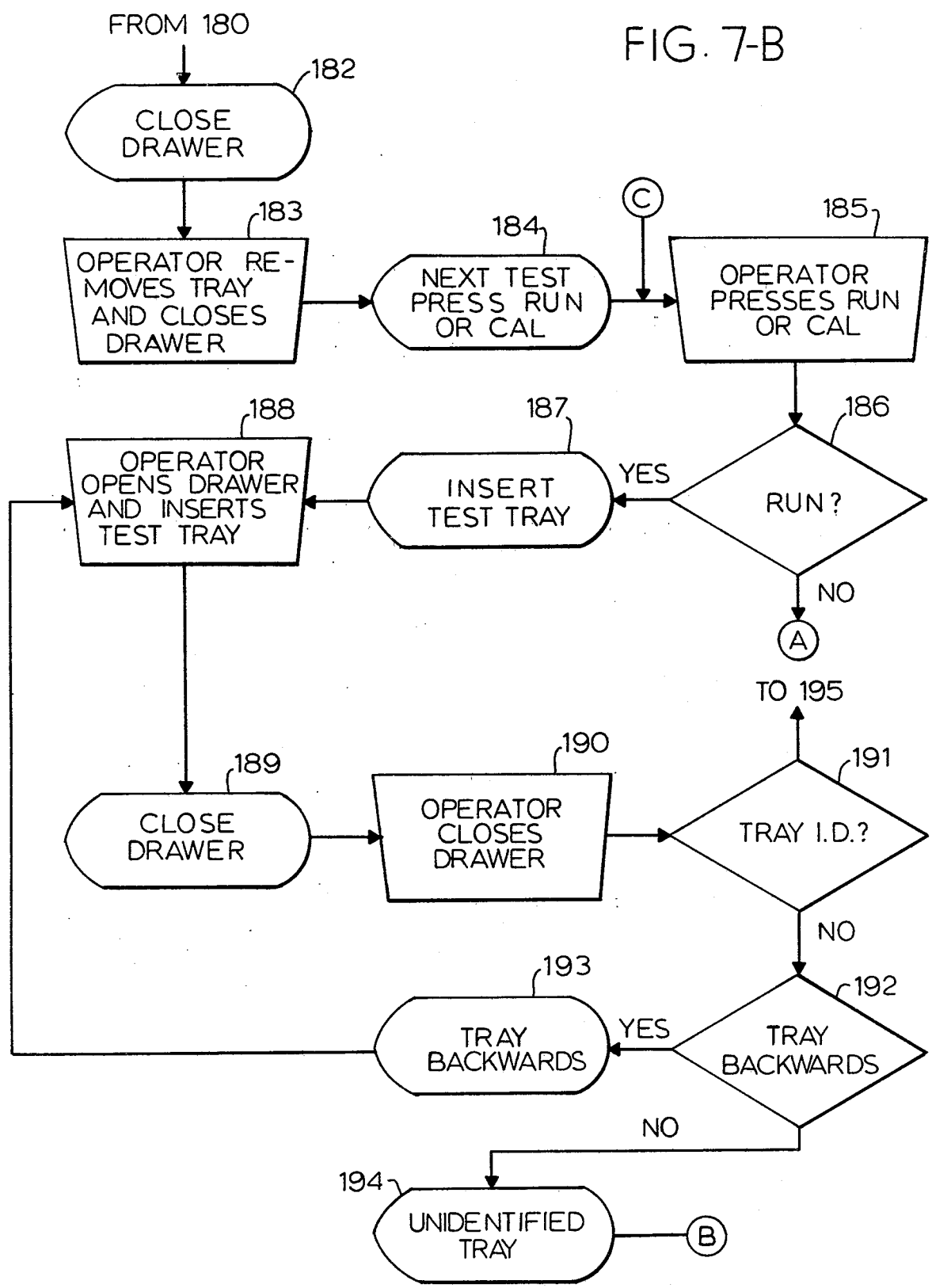
FIG. 7-B

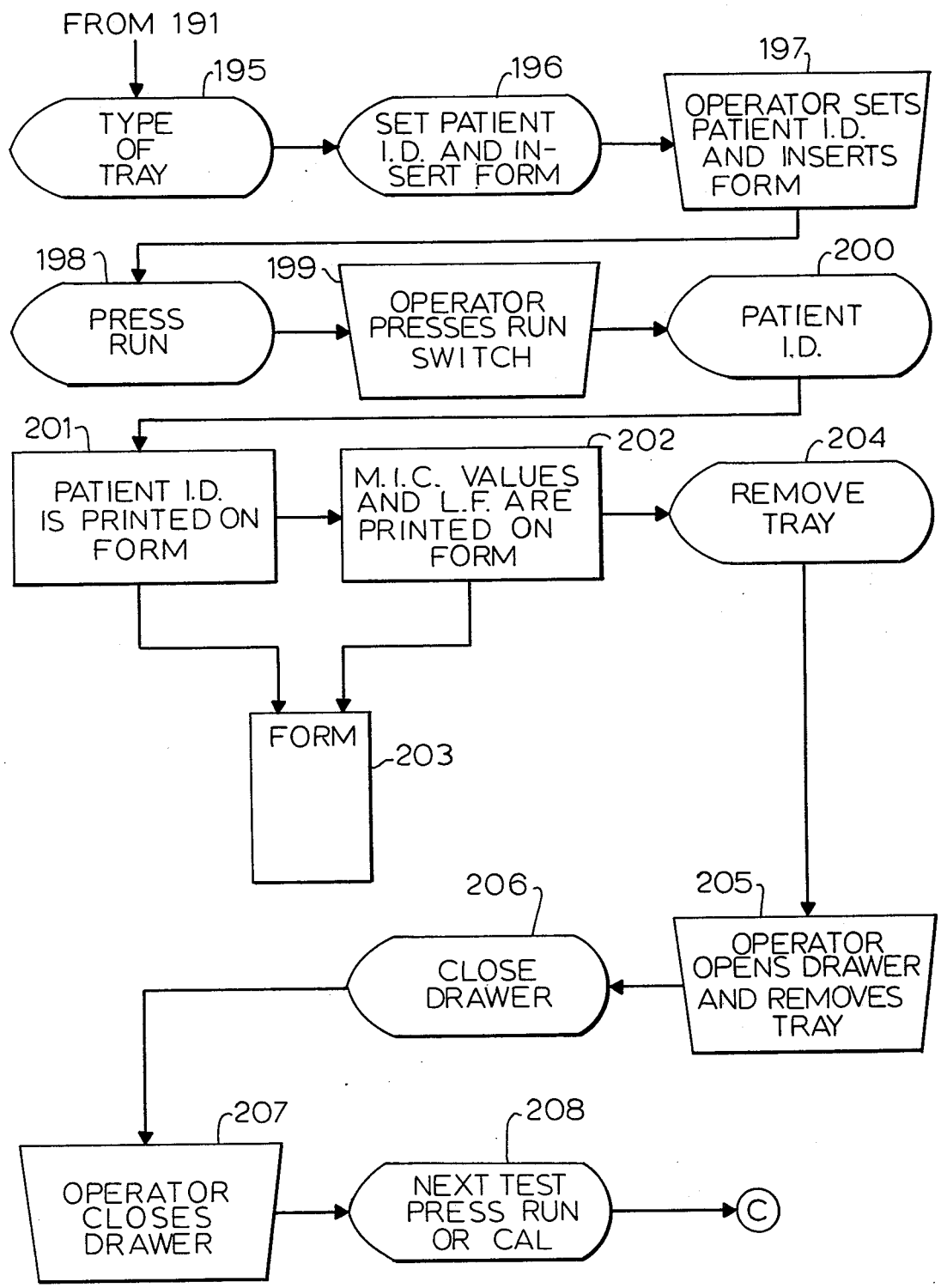
FIG. 7-C

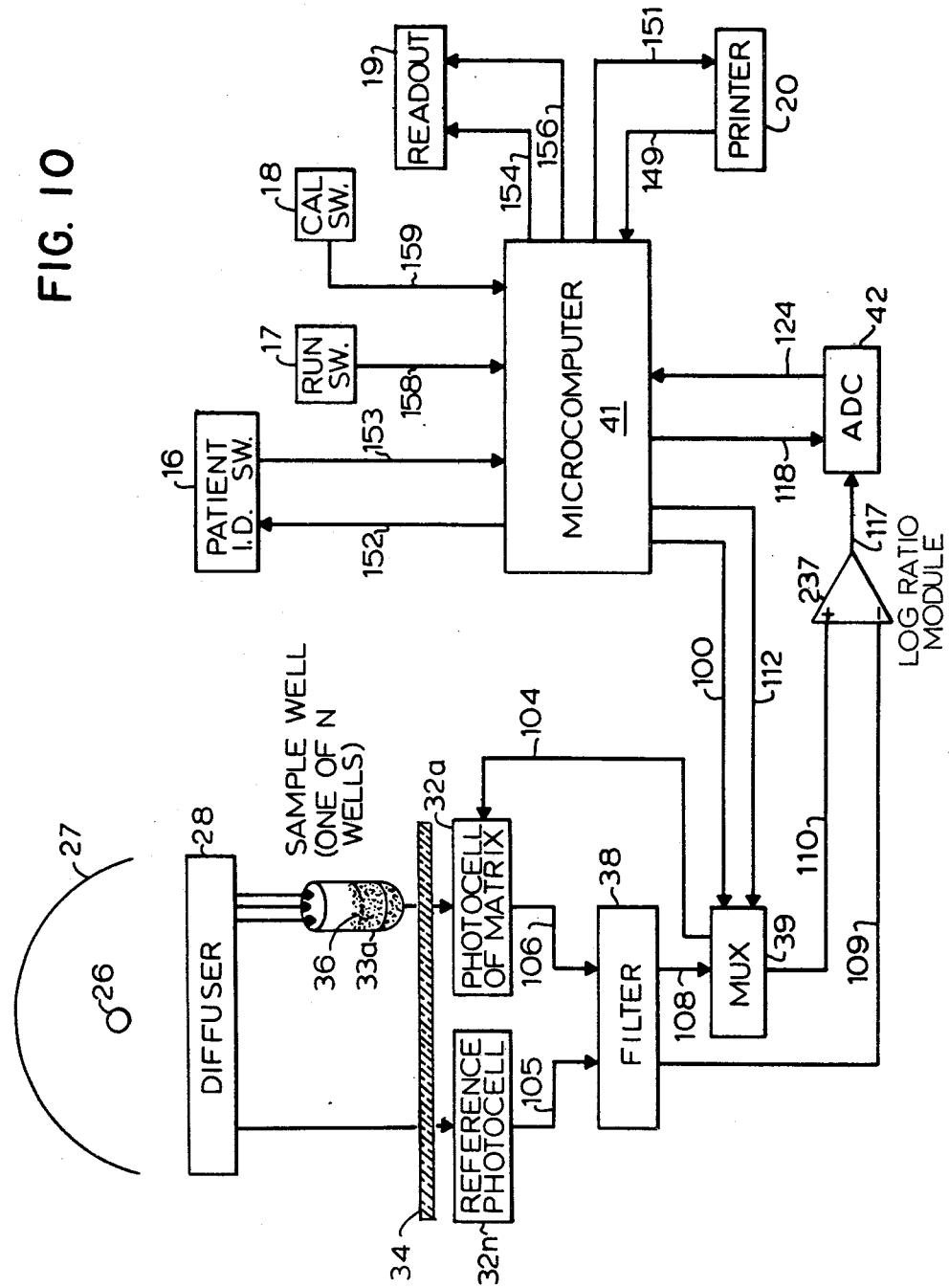

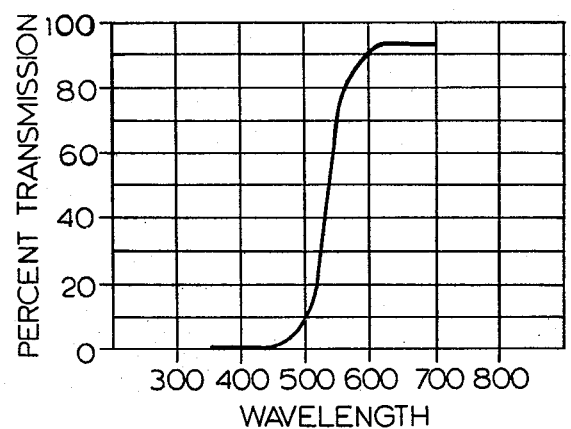
FIG. 14-A
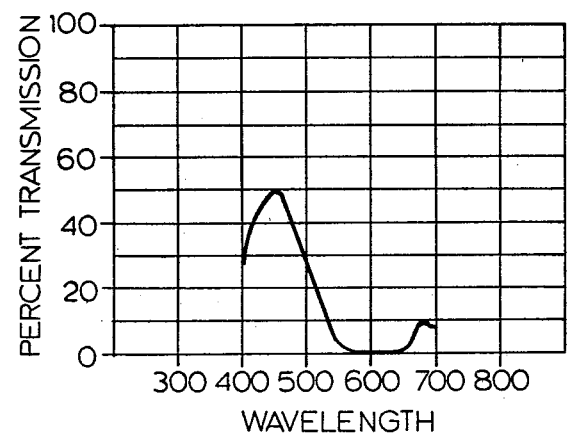
FIG. 14-B
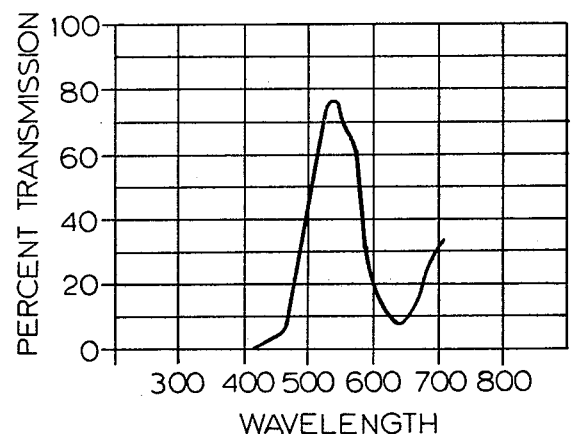
FIG. 14-C

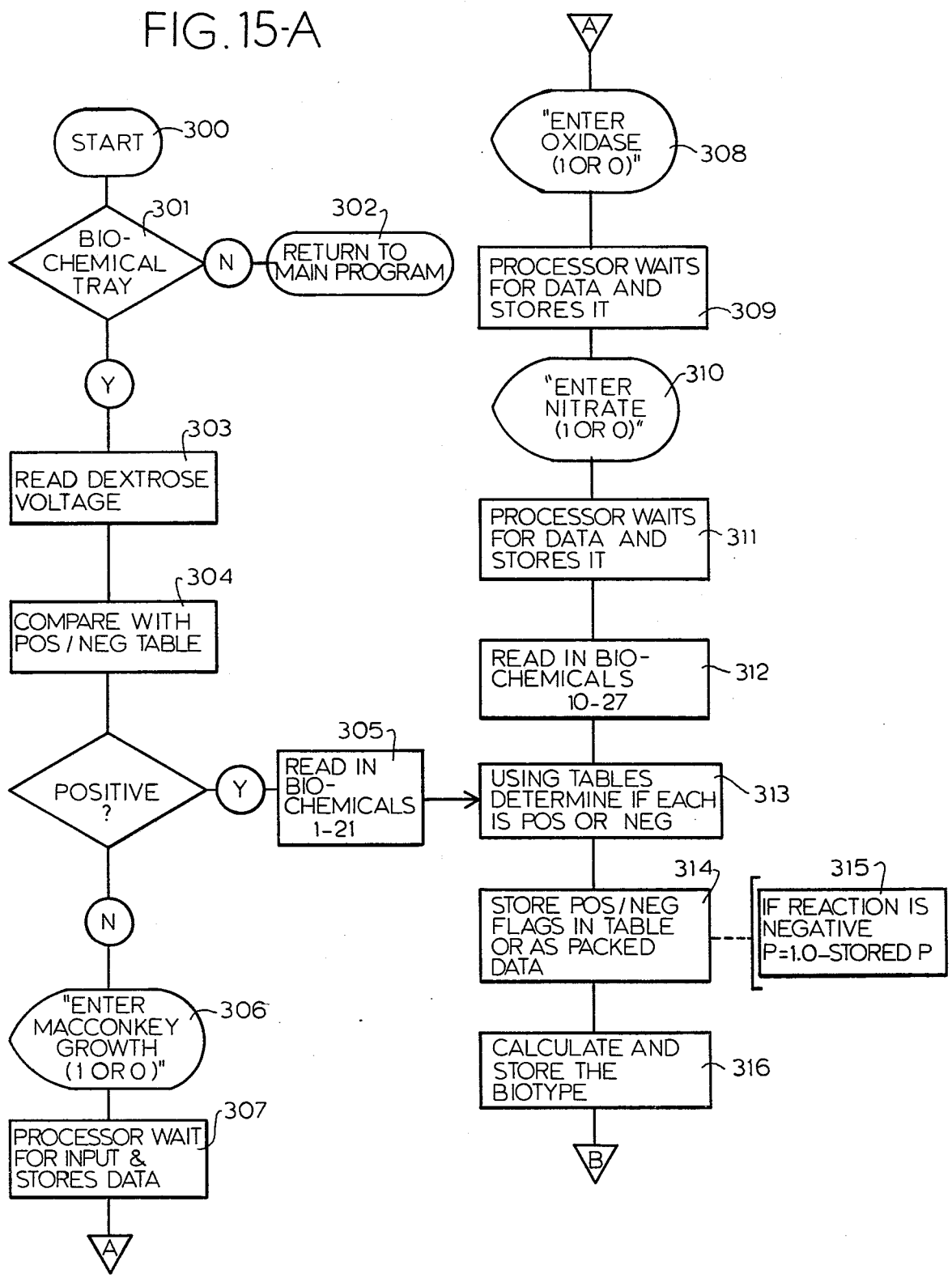
FIG. 15-A

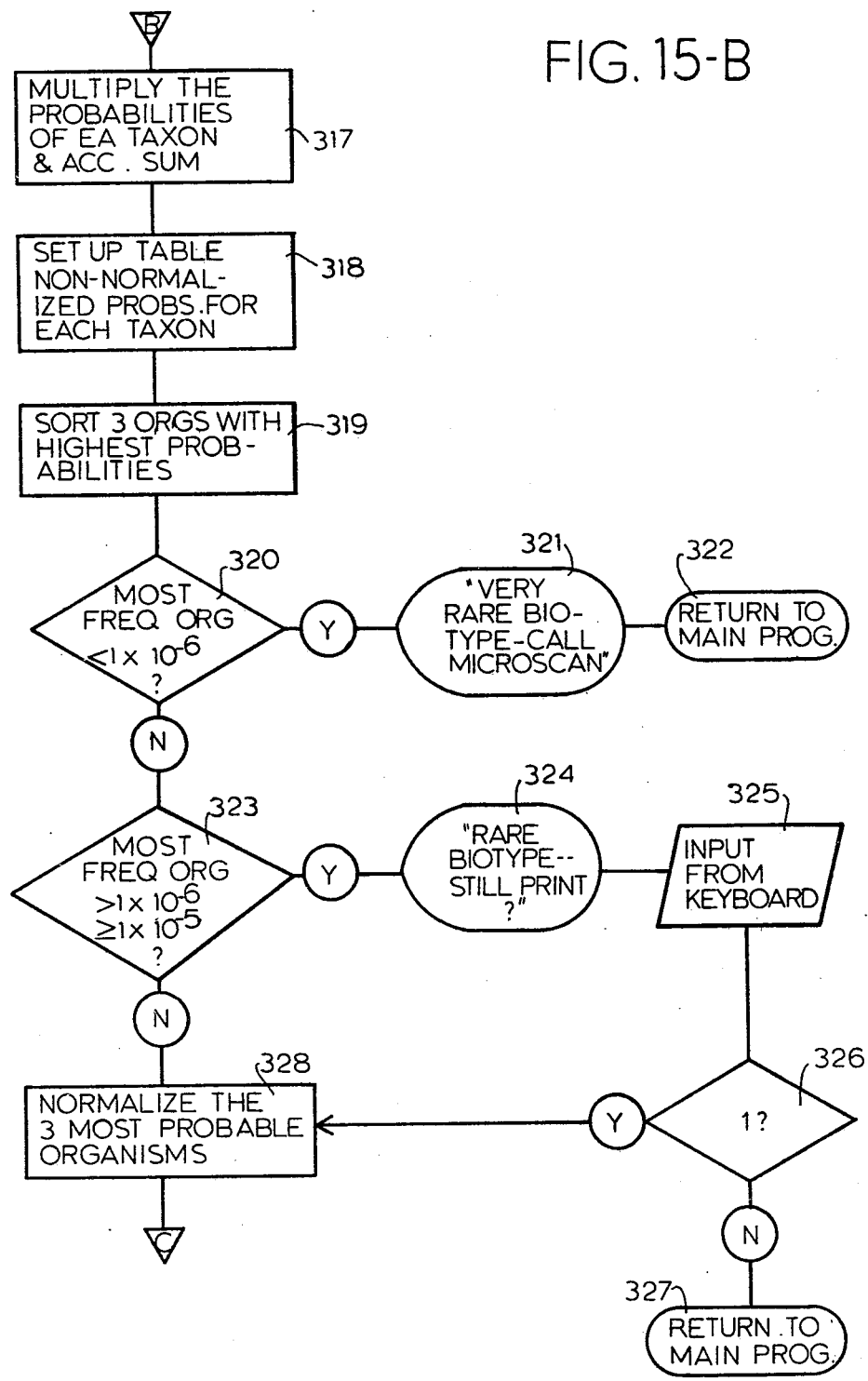
FIG. 15-B

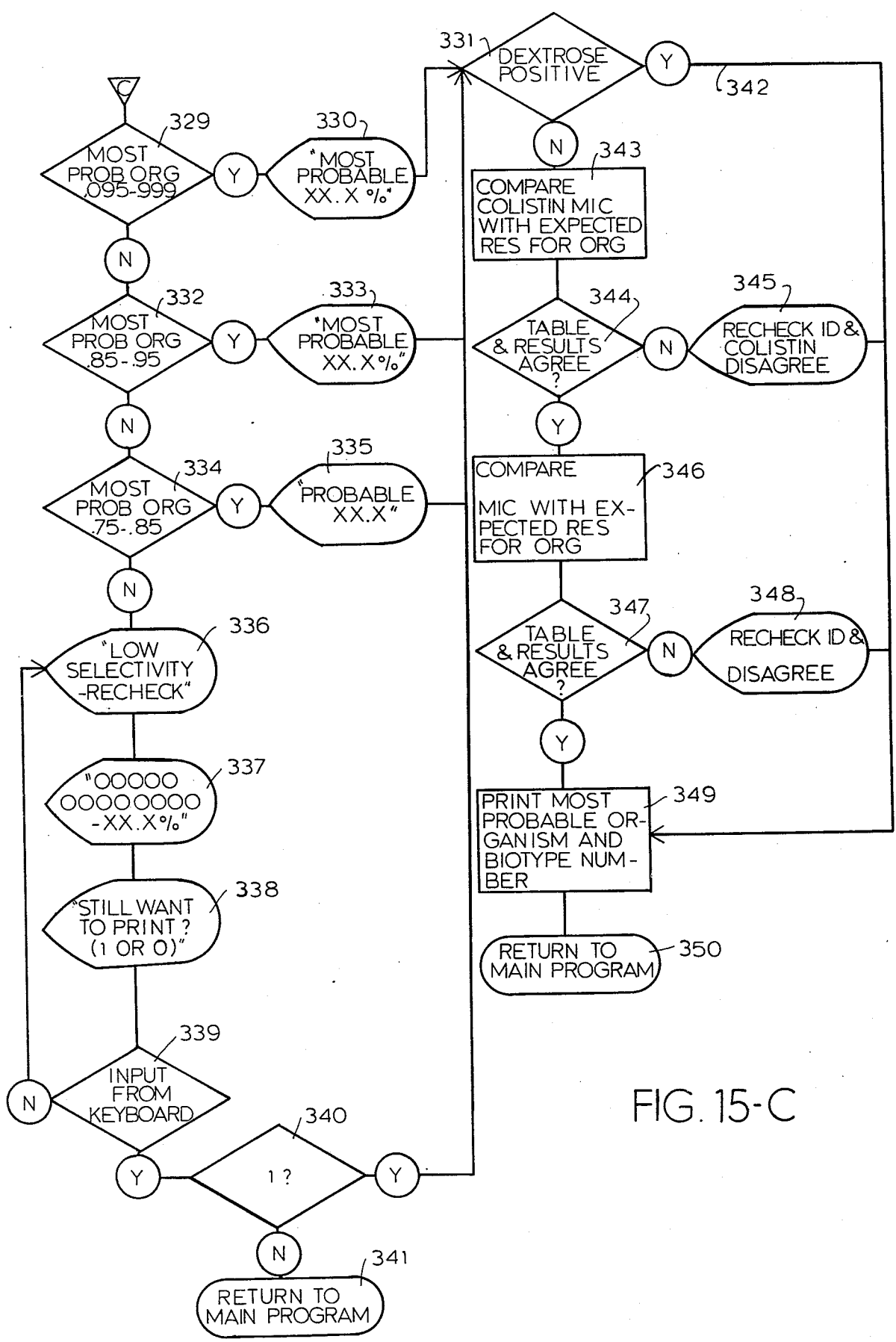
FIG. 15-C

ANTIBIOTIC SUSCEPTIBILITY TESTING

RELATED CO-PENDING APPLICATION

This application is a continuation-in-part of application Ser. No. 891,648, filed Mar. 30, 1978.

BACKGROUND OF THE INVENTION

This invention relates to automatic scanning apparatus, which in rapid sequence performs a series of related densitometric or optical density tests on samples contained in a large number of wells in a tray. It also relates to measurement of the susceptibility of bacteria to different antimicrobic drugs, with automatic quantification of the susceptibility to each drug, so that a physician may select a drug that will most effectively treat an infecting bacterium and choose the appropriate dosage for effective treatment. It further relates to the identification of microorganisms that have been isolated from patients.

In the clinical laboratory, the bacteriology department has two major functions: (1) the identification of organisms that are isolated from patients and (2) the determination of the susceptibility of these organisms to antimicrobic medications. Both of these are involved here.

Identification of microorganisms

Organism identification has generally been accomplished by noting both the microscopic appearance of the bacteria and their gross appearance (colonial morphology) as they grow on a solid medium. In addition to morphologic examination, a technologist sometimes tested the organism with immunological techniques and special stains to gain further information on the microorganism's identity.

However, the most important technique for bacterial identification relates to that organism's biochemical properties.

Each organism possesses a set of enzymes that act as chemical catalysts or fermentors. By performing a series of chemical reactions in a medium where an organism is growing, a technologist is able to identify a combination of positive and negative reactions that effectively provide a chemical fingerprint for that organism. Typically, these reactions include fermentation of a wide range of carbohydrates, citrate utilization, malonate utilization, phenylalanine deaminase production, beta galactosidase production, indole production, hydrogen sulfide production, lysine decarboxylase production, ornithine decarboxylase production, urease production, sucrose utilization, and arginine dehydroxylase production. A reaction result is determined by a visual color change in the medium. The color reagent in most cases is pH indicator which measures the alkalinity or acidity resulting from the chemical reactions. A variety of indicators such as bromphenol blue and phenol red may be used to measure pH changes over a wide range of the pH scale. Another mechanism for chemical color development is the enzymatic splitting of a chromogen (color producing chemical) off the original substrate, thus signalling a positive chemical reaction.

A combination of color reactions as just described forms a profile that may be used to identify the organism. For this purpose, identification can proceed in either a parallel mode in which a large number of tests are performed at one time, or in a serial mode, also known as a sequential or "branching" mode, in which subsequent tests are chosen on the basis of previous results. The serial mode saves reagents since only those tests are performed which will directly affect the final results; however, it is quite time consuming, since each subsequent test cannot be performed until the results from the preceding test have been obtained. In a medical setting, each test may take 24 hours to obtain a result, and where time is of the essence, the system may be far too slow for practical application. Additionally, should the technologist misread one result early in the decision tree, then all subsequent results could possibly be misleading.

For these reasons, the parallel mode employing the performance of a large number of biochemical tests on bacteria is presently preferred by most workers. In the parallel mode, large numbers of known organisms are tested with a battery of biochemical substrates, and the probabilities of each of these bacterial taxa having a positive reaction are tabulated. With this information, the probability of each organism occurring for each combination of chemical reactions can be computed by standard statistical methods.

Systems presently available commercially provide a convenient battery of biochemical substrates and indicators to test a given organism. A "book" (typically a computer printout) is provided to enable a technologist to translate combinations of chemical reactions into the correspondingly most probable organism. These commercial systems provide a plurality of microtubes (e.g., 15 to 30) which contain substrate indicators. The microtubes are inoculated with the bacteria and, after an appropriate time for the organism to grow and elaborate its enzymes, the reactions can be read as a color change. Combinations of these reactions can then be transposed into a unique numerical code.

A standard way of transposing these reactions into numbers involves reading the reactions in groups of threes and expressing the reactions as an octal code. This octal code ranges from 0–7 with 0 representing no positive reaction and 7 indicating that all 3 reactions were positive. This octal number or "biotype" can be found in a book where the most probable organisms are listed for each biotype.

With the present art it is necessary for a technologist to read each reaction visually, record each of the results, compute a biotype number, and then find this biotype number in a computer printout, in order to make the organism identification. Thus, although they are much more convenient than the original serial branching technique the present manual multi-test battery methods are still laborious and time-consuming.

Minimum inhibitory concentration

The physician usually has a choice of about twelve to fifteen types of antimicrobial agents for treating the forty to sixty groups of pathogenic bacteria. Many of these agents are ineffective against a given bacterial strain, but normally some of them will be appropriate for treatment. In order for the physician to choose the best antimicrobic, it is necessary to isolate the pathogenic organism in the laboratory and then test it against a panel of drugs to determine which drugs inhibit growth and which do not. Ideally, the doctor should receive susceptibility information the same day the culture is taken, since it is usually necessary to initiate therapy immediately. Unfortunately, it currently takes one day to isolate an organism, and it has required another day to test the susceptibility of the organism to the antimicrobics. Therefore, it has been customary for the physician to institute therapy based on an educated guess at the time the patient is first seen. If the sensitivity studies completed two days later indicate that the guess was incorrect, therapy is changed to the proper drug.

Clearly an important goal in automating antimicrobic testing would be to diminish the time lag between the initial culture and the obtaining of sensitivity information. An estimated 30 million antimicrobic susceptibility tests are performed annually in the United States by labor intensive manual methods. In addition to the potential economic advantages of automation and obvious advantages to the patient in receiving only the proper treatment, one could also anticipate better precision, quality control and objectivity.

The most frequently used technique to measure antimicrobial susceptibility has been the standardized disc-diffusion method described by Kirby and Bauer (Bauer, Kirby et al., "Antibiotic Susceptibility Testing by a Standardized Single Disk Method", *American Journal of Clinical Pathology*, 1966, Vol. 45, No. 4, p. 493). By this method, isolates of bacteria are grown in suspension to a standardized concentration (usually determined by visual turbidity) and streaked onto nutrient agar (culture medium) in a flat glass Petri dish. Paper discs impregnated with different anti-microbial materials are placed upon the agar streaked with bacteria, and the drug is allowed to diffuse through the agar, forming a gradient halo around the disc. As the bacteria replicate, they form a visible film on the surface of the agar, but in the zones surrounding the antibiotic-impregnated discs, growth is inhibited if the organism is susceptible to that particular antimicrobial agent. Since a concentration gradient has been established, the zone of inhibition around the disc is roughly proportional to the degree of susceptibility. Typically, the laboratory classifies an organism as "sensitive", "intermediate", or "resistant" to each drug in the test panel. Thus the results establish a characteristic profile or "antibiogram" for that organism.

The Kirby-Bauer disc-diffusion method has the advantage of simplicity, but it suffers from several drawbacks. One problem is that of time efficiency. In order that the initial inoculum become visible on the Petri dish so that zones of growth can be distinguished from zones of inhibition, the bacteria numbers must increase by several orders of magnitude over the original number. However, for determination of whether or not the organism is growing in the antimicrobial milieu, which is the only information required, a period that would allow doubling of all the organisms should be theoretically sufficient with suitable detection equipment. For most Gram-negative organisms, the doubling period is between twenty and thirty minutes, following a lag phase. Therefore, an automated system should be able to distinguish growth within a thirty-minute period.

Another difficulty with the Kirby-Bauer disc method is that of standardization. If an organism is "resistant", does that mean that it cannot be treated with higher than normal doses of the microbial agent? Also, how does this information relate to a site in the body where the antimicrobic is concentrated (such as bile) or decreased in amount (such as cerebrospinal fluid)?

To answer these questions, quantitative data are necessary. To obtain quantitative results, it must be determined what minimum concentration of a drug will inhibit the organism's growth. This quantitation of susceptibility is known as minimum inhibitory concentration or MIC. The MIC may be determined by making serial dilutions of the drug in agar or broth, and then inoculating each dilution of each drug with a standardized suspension of bacteria. Since the test procedure may involve as many as 70 to 80 individual tubes, it can become a formidable task if the test is performed in individual test tubes on a macro scale. Systems are available in which the individual dilutions of antimicrobics are made in plastic trays containing small microtubes. (March and MacLowry, "Semiautomatic Serial-Dilution Test for Antibiotic Susceptibility", *Automation and Data Processing in the Clinical Laboratory*, Springfield, Ill., C. C. Thomas 1970). Organisms can be inoculated in a single step using a multi-pronged template. Thus, setting up the test is simplified, and it takes slightly less time to provide quantitative data than qualitative Kirby-Bauer information. There are now semiautomated devices that dispense antimicrobial solutions into the microtubes. Trays of microtubes are also commercially available with frozen solutions in the tubes, and the Gram-negative antimicrobial panels have been combined with biochemical tests to identify enteric bacteria as well as to determine their antimicrobic susceptibility.

Although MIC results give quantitative information which allows consideration of multiple doses and multiple sites, the MIC numbers in themselves can be confusing to the clinician. To use MIC data correctly, a physician must refer to tables of achievable antimicrobic levels as a function of dosage and body site. Therapy will be effective if the achievable drug level for a particular dose and site in the body is two to four times the MIC. With the present invention described below, such interpretation of MIC data is accomplished by a computer, which compares the MIC with a table of achievable drug levels at different body sites and different doses.

Optical testing methods and apparatus

Optical detection methods have been suggested and have proven to be powerful tools to measure bacterial growth. A laser light-scattering system can have the sensitivity to detect a single bacterium. Optical methods measure the presence of bacteria either by nephelometry or turbidity measurements. Nephelometry measures the ability of the bacteria particles to scatter light, and the detector is aligned at an angle to the axis of the light source. Turbidity measures the net effect of absorbance and scatter, and the transducer is placed on the axis of the radiation source. Nephelometry measurements are significantly more sensitive than turbidity measurements, but since the nephelometer measures only that fraction of light scattered by bacteria, the signal to the detector is small, and both light source and transducer amplification must be correspondingly large.

Some apparatus heretofore relied direct inspection by the human eye, as did Astle in U.S. Pat. No. 3,713,985. Aware of inaccuracies involved, Astle suggested, but did not disclose details of automatic equipment for reading and recording the results of densitometric tests and suggested that his turbidity data could be fed to a device that would translate the data to machine language for recording on computer punch cards. Astle does not teach how to do that. His own device is a strip having a series of wells, all in a single line which involve mechanical position shifts.

Automation in microbiology has lagged far behind chemistry and hematology in the clinical laboratory. However, there is presently an intensive effort by industry to develop this field. The best publicized devices for performing automated antimicrobic susceptibility testing use optical detection methods. A continuous flow device for detecting particles 0.5 micron or less has been commercially available since 1970; however, probably due to its great expense, it has not been widely used in the laboratory. Other devices using laser light sources have been suggested but have not proven commercially practicable. Recently, the most attention has been directed to three devices discussed below.

The Pfizer Autobac 1 system (U.S. Pat. No. Re. 28,801) measures relative bacterial growth by light scatter at a fixed 35° angle. It includes twelve test chambers and one control chamber in a plastic device that forms multiple contiguous cuvettes. Antibiotics are introduced to the chambers via impregnated paper discs. The antimicrobic sensitivity reader comes with an incubator, shaker, and disc dispenser. Results are expressed as a light scattering index (LSI), and these numbers are related to the Kirby-Bauer "sensitive, intermediate and resistant." MIC measurements are not available routinely with this instrument. In a comparison with susceptibilities of clinical isolates measured by the Kirby-Bauer method, there was 91% agreement. However, with this system some bacteria strain-drug combinations have been found to produce a resistant Kirby-Bauer zone diameter and at the same time a sensitive LSI.

The Auto Microbic System has been developed by McDonnell-Douglas to perform identification, enumeration and susceptibility studies on nine urinary tract pathogens using a plastic plate containing a 4×5 array of wells. See Gibson et al., U.S. Pat. No. 3,957,583; Charles et al., U.S. Pat. No. 4,118,280, and Charles et al., U.S. Pat. No. 4,116,775. The specimen is drawn into the small wells by negative pressure and the instrument monitors the change in optical absorbance and scatter with light-emitting diodes and an array of optical sensors. A mechanical device moves each plate into a sensing slot in a continuous succession so that each plate is scanned once an hour, and an onboard digital computer stores the optical data. The system will process either 120 or 240 specimens at a time. One can query the status of each test via a CRT-keyboard console, and hard copy can be made from any display. When the system detects sufficient bacterial growth to permit a valid result, it automatically triggers a print-out. Following identification in four to thirteen hours, a technologist transfers positive cultures to another system which tests for antimicrobic susceptibility. The results are expressed as "R" (resistant) and "S" (susceptible); no quantitative MIC data are provided.

It should be noted that Gibson et al., U.S. Pat. No. 3,957,583 do not include automation, but use naked-eye inspection or a manually-operated colorimeter. Scanning is therefore a hand or a mechanical operation. Charles et al., U.S. Pat. Nos. 4,116,775 and 4,118,280 also require mechanical movement of their cassette for reading different rows.

The Abbot MS-2 system consists of chambers composed of eleven contiguous cuvettes. Similar to the Pfizer Autobac 1, the antimicrobial compounds are introduced by way of impregnated paper discs. An inoculum consisting of a suspension of organisms from several colonies is introduced into the culture medium, and the cuvette cartridge is filled with this suspension. The operator inserts the cuvette cartridge into an analysis module which will handle eight cartridges (additional modules can be added to the system). Following agitation of the cartridge, the instrument monitors the growth rate by turbidimetry. When the log growth phase occurs, the system automatically transfers the broth solution to the eleven cuvette chambers; ten of these chambers contain antimicrobial discs, and the eleventh is a growth control. The device performs readings at five-minute intervals, and stores the data in a microprocessor. Following a pre-set increase of turbidity of the growth control, the processor establishes a growth rate constant for each chamber. A comparison of the antimicrobic growth rate constant and control growth rate constant forms the basis of susceptibility calculations. The printout presents results as either resistant or susceptible; if intermediate, susceptibility information is expressed as an MIC.

Non-optical methods have also been used or suggested for measuring antimicrobic sensitivity in susceptibility testing. These have included radiorespirometry, electrical impedance, bioluminescence and microcalorimetry. Radiorespirometry, based on the principle that bacteria metabolized carbohydrate and the carbohydrate carbon may be detected following its release as $CO_2$, involves the incorporation of the isotope $C^{14}$ into carbohydrates. Released $C^{14}O_2$ gas is trapped and beta counting techniques are used to detect the isotope. The major difficulty in applying the isotope detection system to susceptibility testing, however, is that an antimicrobic agent may be able to stop growth of a species of bacteria, yet metabolism of carbohydrate may continue. Less likely, a given drug may turn off the metabolic machinery that metabolizes certain carbohydrates, but growth may continue. This dissociation between metabolism and cell growth emphasizes the fact that measurements for detecting antimicrobic susceptibility should depend upon a determination of cell mass or cell number rather than metabolism.

The electrical impedance system is based on the fact that bacterial cells have a low net charge and higher electrical impedance than the surrounding electrolytic bacterial growth media. A pulse impedance cell-counting device can be used to count the cells; however, available counting devices are not designed to handle batches of samples automatically, and generally do not have the capacity to distinguish between live and dead bacterial cells. Another approach with electrical impedance has been to monitor the change in the conductivity of the media during the growth phase of bacteria. As bacteria utilize the nutrients, they produce metabolites which have a greater degree of electrical conductance than the native broth, so that as metabolism occurs, impedance decreases. However, since this technique measures cell metabolism rather than cell mass, its applicability to antimicrobic susceptibility detection suffers from the same drawback as radiorespirometry.

Bioluminescence has also been suggested for the detection of microorganisms. It is based on the principle that a nearly universal property of living organisms is the storage of energy in the form of high energy phosphates (adenosine triphosphate, ATP), which can be detected through reaction with firefly luciferase. The reaction results in the emission of light energy which can be detected with great sensitivity by electronic light transducers. Although a clinical laboratory may obtain a bioluminescence system to detect the presence of bacteria in urine, the technique is expensive due to the limited availability of firefly luciferase, and problems have been encountered in standardizing the system.

Microcalorimetry is the measurement of minute amounts of heat generated by bacterial metabolism. The principle exhibits certain advantages, but laboratories have not adopted such a system, one serious drawback being that the system measures metabolic activity rather than bacterial mass or number.

SUMMARY OF THE INVENTION

The present invention employs optical methods and apparatus for automatically identifying microorganisms and automatically determining bacterial susceptibility to a number of different antimicrobic drugs, utilizing turbidimetry.

The apparatus of the invention employs a sample tray having a series of wells, e.g., 80 or 96 wells, for containing samples, the wells having translucent bottoms. The apparatus has tray holding means for holding the tray accurately in a predetermined position without blocking off light paths through the wells. A light source means, preferably a single source of diffuse light, is positioned above the sample tray, sending light down through all the wells at roughly the same intensity. Collimation means, preferably beneath the tray holding means, collimates the light from each well after it has passed through the wells. For some tests there is light filter means below the tray holding means, for filtering the color values of the light passing through the wells.

The light paths from the cells terminate at an array of light-intensity-detecting photocells, one adjacent to each well. A reference detecting photocell receives light directly from the light source means without passing through a said tray, or at least without passing through a sample.

A sequential signal-receiving means is connected to all the photocells for receiving sequentially a signal from each photocell in a prescribed order, each signal corresponding to the intensity of light received at the photocell. Electronic sequencing means is connected to the signal-receiving means and electronically causes it to receive its signals in order, all without any mechanical movement of anything.

First comparator means is connected to the signal-receiving means and sequentially compares the signal from each photocell of the array with the signal from the reference-detecting photocell and then develops a different signal therefrom.

Data storage means holds data values corresponding to zero reaction or other base comparison values and holds data relating to various organisms or tests. Second comparator means is connected to the first comparator means and to the data storage means, and sequentially makes a comparison of each different signal value with a value corresponding to that of the same well when empty or at zero time or zero growth or reacts or develops a resultant value from that comparison.

Third comparator means may be connected to the second comparator means and to the data storage means sequentially compares said resultant values with a large number of stored values and for determining such conclusory values as the probability values for the presence of selected organisms in the sample or the minimum inhibitory concentration desired.

Finally, output means connected to the third comparator means gives the results obtained. It may display them or print them out.

The present invention makes it possible to use an optical-electrical method for automatically reading the color changes of a plurality of biochemical reactions in small microtubes and for calculating and printing out the most probable organism by means of an inboard computer and probability data stored in the computer memory.

The microtubes are, preferably, all part of a unitary sample tray, made of suitable translucent material. Each microtube is a well of this tray. In each well and in a standardized manner, is placed a suitable chemical reagent or reagents; then each well is inoculated with the sample. Photodetection of color changes is accomplished by the passage of uniform intensity light through each of the wells and through the translucent well bottoms following an incubation period. At the opposite side of the tray, preferably below the tray, is an optical fiber designed to pass only certain wavelengths of light. Beneath the filter is an array of sequentially-scanned transducers such as photoelectric cells, one associated with each well. The optical filter is designed so that a shift in color in the wells will result in a predictably greater or lesser amount of light passing through to the photoelectric cells.

Previously, the reading of an identification system required a technologist manually to record visual impressions of color changes indicating either positive or negative biochemical reactions generated by the enzymes contained in the bacteria to be tested. The apparatus in the present invention provides this reading automatically and objectively. With present manual methods and apparatus, after the reactions had been determined, it was necessary for the technologist to calculate a numerical summation of these reactions and to express them as an octal number or "biotype". This biotype number was then searched out in a large book containing various biotypes and corresponding organism probabilities. Once a biotype was found, the most probable organism was noted and reported. With the present invention, the computer which is an integral part of the instrument, computes the probability for each organism and prints out the identification on a laboratory form.

Signals from the transducers (photoelectric cells) are transmitted to a computer which contains an algorithm that transforms the reaction results to organism identification. The following description presents in detail the algorithm used by the computer to convert the reaction colors to organism identification. This algorithm is also summarized in the accompanying flow diagram.

For each biochemical reaction, a voltage value, which discriminates between a positive and negative result, is or has already been determined by experimentation. Each of these "cuttoff" points is stored in the computer's memory together with a module that indicates if a given value above that print is negative or positive.

The computer is programmed to compile a table of the probability of occurrence for each biochemical reaction with each of the organisms (taxa) in the data base. This probability assumes a positive reaction. If, in fact, a negative reaction occurs, then the probability of the observation would be 1.000-P. For example, if a given biochemical with a given organism has a probability of 0.005 of occurring, and the reaction was found to be negative, then the probability would be 0.995 (1.000-0.005) that this reaction would not occur. So the program at this point calls for converting all the negative probabilities to 1.000P values for the table. The positive reactions are left unchanged, and are manipulated exactly as they occur in the table.

In addition to printing out the most probable organism, the instrument provides the operator with several indices of reliability. First, the overall non-normalized probability of the reaction is computed. If this probability is very low, this may mean that there was an error in reading or that the suspension of test bacteria contained more than one taxon. Second, the relative normalized probabilities of three most likely organisms are computed and displayed to the technologist. Clearly, if several organisms have equal probability of occurring with a given set of biochemical reactions, further testing is necessary to discriminate between them. Third, the instrument measures the susceptibility of the test organism to several antimicrobics. If the known susceptibility is in conflict with the identification by biochemicals, a warning is given to the operator.

Thus, after the individually observed probabilities have been determined, each of the biochemical probabilities is cumulatively multiplied by the other probabilities for a given taxon. For example, the observed probability (P) for the organism, E. Coli, with dextrose is multiplied by the P for sucrose, and this product is multiplied by the P of sorbitol, and so on. This continues until a product of, for example, twenty-one multiplications is obtained for each organism. Each of these products is the non-normalized frequency for each taxon. As these non-normalized frequencies are being computed, they are added to each other, so that a sum of all of the non-normalized frequencies for each organism is obtained.

Rare combinations of biochemical reactions can occur with organisms, but more commonly, a very low frequency will indicate a technical error. The most common technical errors are due either to a mixed culture or to a reading error. The instrument software is designed so that an organism frequency (non-normalized) of less than $1 \times 10^{-6}$ will be read out as unacceptable. If the organism with the greatest frequency is computed to have a frequency of less than this value, the display indicates: "VERY RARE BIOTYPE", and the program goes back to the beginning. If the first organism frequency is greater than $1 \times 10^{-6}$ but less than or equal to $1 \times 10^{-5}$, the display says: "RARE BIOTYPE-PRINT? (1 or 0)". If the operator wishes to go ahead and print, then he presses "1" on the keyboard; if he wishes to go back to the main program, then he presses "0". The instrument waits for either of these keys to be pressed.

Normalization is accomplished by dividing each of the three highest frequencies by the sum of all of the frequencies. If the most probable organism has a normalized frequency between 0.950 and 0.999, then the display shows "MOST PROBABLE—XX.X%". In this case, the probability is converted to a percent figure. The program then returns to check the dextrose fermenter flag. If the organism is a dextrose fermenter, then the program goes on to print the name of the most probable organism and the biotype in appropriate spaces on the form. If it is a non-fermenter it is compared with Colistin and nitrofurantoin (Furadantin) results, as outlined below. If the most probably organism has a normalized frequency between 0.850 and 0.950, then the display indicates "VERY PROBABLE—XX.X%". The program again checks for fermenter or non-fermenter status as above. If the relative (normalized) frequency is between 0.750 and 0.850, the display indicates: "PROBABLE—XX.X%" and loops through the fermenter/non-fermenter check as above. If the relative probability is less than 0.750, the display outputs three messages in sequence at one-second intervals: "LOW SELECTIVITY-RECHECK"; followed by "000000000000000000000—XX.X%" where 000 is the organism name, and XX.X is the percentage as above. The third display is "STILL WANT TO PRINT? (1 or 0)".

As stated above, if the organism is a non-fermenter, the instrument also measures the susceptibility of the test organism to several antimicrobics. Thus, identification may be evaluated for its sensitivity to the two antibiotics Colistin and Nitrofurantoin. If there is growth in these wells (hex voltage less than threshold), then this means the organisms are resistant ("R"). If there is no growth (hex voltage greater than threshold), then the organism is sensitive or "S".

Once the sensitivity or resistance for Colistin has been determined, the program looks up a table to see if the result is correct; if not, then it displays on the visual display: "RECHECK I.D. & COLISTIN DISAGREE"; the most probable organism is then printed out, and the routine returns to the main program. If the table and results agree with Colistin, then a similar procedure is performed with Nitrofurantoin. If there is disagreement, the display says: "RECHECK-ID & FURANTOIN DISAGREE." If there is agreement, then the result is printed out as above.

In the method for determining bacterial susceptibility to various antimicrobic drugs, the system of the invention uses broth-dilution to determine susceptibility. Serial dilutions of the antimicrobic agent are inoculated with the organism and incubated for a period sufficient to allow detectable growth. The apparatus of the invention determines minimum inhibitory concentration (MIC) of a particular antimicrobic drug, which is the lowest concentration of that drug that results in no detectable bacterial growth. Typically, ten antimicrobic drugs are evaluated, with seven different dilutions of each drug being tested. Therefore, to obtain an MIC determination for ten drugs, seventy tubes or wells must be inoculated and examined. In contrast to previous methods using individual full-sized test tubes, which were cumbersome and expensive, the present system utilizes "micro-tubes", which are presently available as disposable, molded plastic trays, each well of which holds approximately 0.5 milliliter.

For measurement of the MIC values in these trays, appropriate dilutions of each antibiotic must be placed in the wells or micro-tubes. Semiautomated devices for making the dilutions and filling the trays in large batches are available commercially. Alternatively, a laboratory may obtain trays that are already filled with antibiotic dilutions and kept frozen until use. To prepare the bacteria cultures for inoculation into the wells, a suspension of the bacterial organisms in water is made in a container. By means of a multiple-pronged device, a technician is able to inoculate a uniform drop of bacterial suspension into each of the large plurality (e.g., seventy) of wells with a single motion. The bacteria and the various dilutions of the antimicrobic agents are incubated for a time period sufficient to produce detectable bacterial growth, and the MIC may then be determined as the lowest concentration of the effective antimicrobic agents in which there is no evidence of growth.

Previously the reading of such an MIC tray was done by manual viewing performed by a technician, and was a laborious procedure. An overnight incubation period was generally required in order to produce visually detectable patterns of growth. However, the apparatus and method of the present invention provide for the performance of the reading and interpretive task automatically. Moreover, the device has the capability of interpolating the MIC between twofold dilutions whereas by visual reading a technician can only detect the difference between growth and no growth and thus can only read MIC to the nearest twofold dilution. With the sensitive photoelectric apparatus described herein, together with the capabilities of a microcomputer the different gradations of growth can be measured even after a relatively short incubation period, and a precise MIC can be calculated and displayed on a screen or printed out. Thus, the device makes available continuous numerical data that improves accuracy and allows quantitative quality-control techniques.

Photodetection of bacterial growth is accomplished by passage of uniform intensity light through each of the wells and through the translucent well bottoms following the incubation period. The uniform light may be obtained from plural uniform sources, one at each well, or by a single source of uniform, diffused light over the entire tray. At the opposite side of the tray, preferably below the tray, are an array of sequentially-scanned photoelectric cells, one associated with each well. The sensed light intensity level at each well is compared by computer with a light level corresponding to zero bacteria growth to determine a relative value of turbidity. The reference value may be obtained by the reading of a sterile control well.

In addition to the quantitative MIC data, the apparatus and method of the invention provide a graphic interpretive printout to guide the physician's therapy. The computer is programmed to translate the MIC value into dosage ranges that would be necessary to achieve blood levels of the antimicrobic drug effective to inhibit growth of the organism at a particular site. For example, a printout of "−" might be used to indicate that the organism is resistant and no dosage of a drug can effect the organism. A printout of "+" may be used to mean that the organism is resistant and may respond to high intramuscular or intravenous doses, with "++" indicating intermediate sensitivity and that the organism may respond to higher than recommended doses. A printout of "+++" would indicate that the organism may be sensitive to the usual doses of an antibiotic, and "++++" would indicate a high degree of sensitivity and thus an optimal drug with which to treat the infectious agent.

In one embodiment, a method according to the invention for determining susceptibility of a bacteria culture to various antimicrobic drugs and of determining the minimum inhibitory concentration (MIC) of the bacteria culture to those drugs to which it is susceptible comprises the steps of placing the plurality of different antimicrobic drugs in a plurality of wells in a light-transmissive tray, each drug being included in a series of wells in serially-diluted known concentrations; establishing a known uniform concentration of the bacteria and placing the uniform concentration in equal volumes of the wells; following an incubation period, passing light in substantially equal intensity through each well and determining a turbidity value for the bacterial suspension of each well by sequentially sensing the intensity of light transmitted through the bacterial suspensions of the wells by means of photodetectors adjacent to the wells opposite the light source; and in a computer, comparing turbidity values with a turbidity value corresponding to zero bacterial growth, thereby determining which antimicrobic drugs have inhibited bacterial growth and the minimum concentration of each inhibitory drug required to inhibit growth, and displaying the determined information. The concentration of the bacteria culture may itself be initially determined by turbidimetric measurement utilizing a light source and at least one photodetector. The antimicrobic drugs may be placed in the tray in a rectangular matrix of wells, with each column of wells containing incrementally varying concentrations of a single drug. Of course, any arrangement of the wells or of the antimicrobics in the wells is suitable, so long as the computer has the proper information as to what is being tested in each well. Control wells containing only the bacterial suspension, as well as sterile control wells, may be included for selfchecking of the system and/or providing a transmitted light value corresponding to zero bacteria growth. The system may, as explained above, provide for translation of the MIC values to dosage ranges necessary to establish the required antimicrobic concentration at the body sites involved.

There are other applications for the instrument. For example, heretofore, very sensitive techniques have used bacteria as biological indicators for detecting trace amounts of chemicals. Strains of bacteria are obtained by mutation that manifest growth that is directly proportional to the quantity of a given substance so that calibration curves are easily made. Such a substance and the amount thereof can therefore be detected in a cultured sample by using the apparatus of the invention, preferably using optical filters. Suitable programs can, of course, be preferred.

Another example is the instrument's applicability to the technique of enzyme-linked immuno absorbent assay (ELISA) to detect the presence of a specific species of protein molecules (e.g., bacteria, virus, or hormone) which is detected by its combination with an antibody. An antigen-antibody reaction is detected (in this technique) by a color change caused by an enzyme or enzymes and detected by the instrument.

BRIEF DESCRIPTION OF THE DRAWINGS

In the drawings:

FIGS. 7A, 7B, and 7C are flow charts of operational steps involved in the method of determining minimum inhibitory concentration.

FIG. 10 is a block diagram similar to FIG. 4, showing a modified form of the invention as used for determining minimum inhibitory concentration.

FIGS. 14A, 14B and 14C comprise a set of three spectral absorbent responses for three respective optical filters that may be used in the invention.

FIGS. 15A, 15B, and 15C are flow charts of operational steps involved in the method for identifying microorganisms according to the principles of the invention.

DESCRIPTION OF THE PREFERRED EMBODIMENTS

The apparatus of FIGS. 1–6

Figure 1:
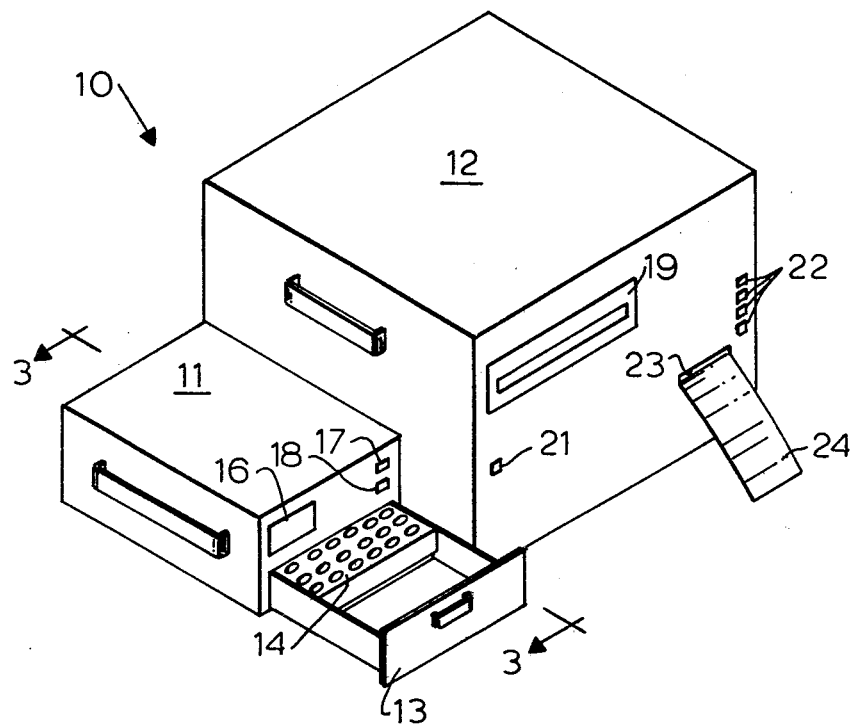
FIG. 1 is a perspective view showing an automated apparatus embodying the principles of the invention.

FIG. 1 shows one example of an external configuration which the susceptibility testing apparatus 10 of the invention may take. The unit 10 comprises a photo unit or optical detection unit 11 and a processor unit 12. The optical detection unit 11 preferably includes a drawer 13 for receiving, supporting, and correctly positioning a sample tray 14 which is examined by detection apparatus of the unit 11 when the drawer is closed and the testing operation is begun. The detection unit 11 may also include a patient identification input switch 16, a run switch 17 and a calibrate switch 18. The processor unit 12 may include a readout display 19, an on/off power switch 21, printer control buttons 22, and a printout exit 23 which dispenses a printed "ticket" 24 bearing the desired susceptibility information.

Figure 2:
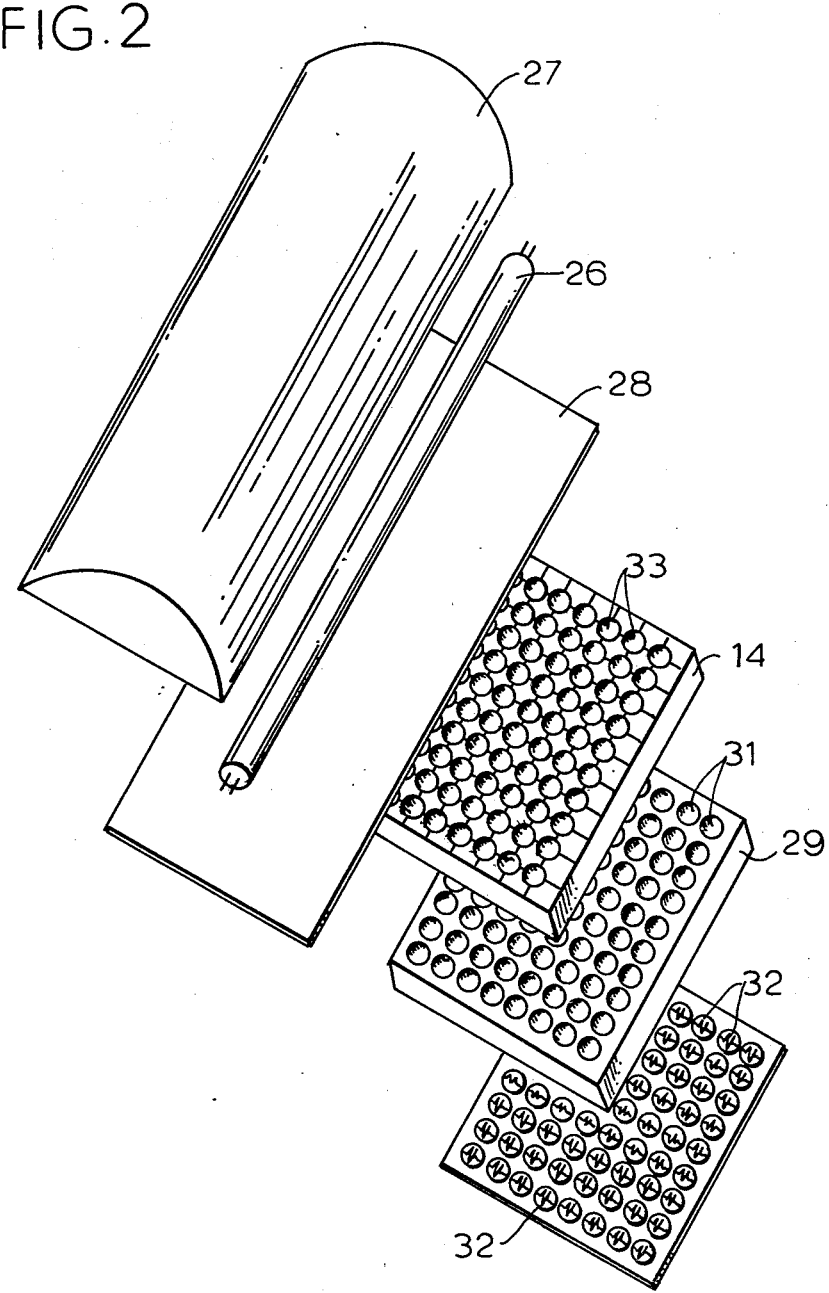
FIG. 2 is an exploded perspective view showing a sample tray and optical detection equipment forming a part of the apparatus of FIG. 1, as used in determining antibiotic susceptibility.

FIG. 2 somewhat schematically represents the configuration of the detection apparatus associated with the optical detection unit 11 of the apparatus 10. Within the detection unit 11 above the drawer 13 is a source of uniform, diffuse light which may comprise, for example, a fluorescent light bulb 26, a parabolic reflector 27 positioned thereabove such that the lamp 26 is at the focal point of the reflector 27, and a diffuser 28 just below the lamp and reflector. The arrangement of the lamp 26 and the reflector 27 provides a nearly uniform distribution of light over the surface of the diffuser 28, and the diffuser improves uniformity and reduces intensity to the desired level.

Within the drawer 13 are a sample tray holder 29 having a matrix of openings 31, and an array of photocells 32 therebelow in a matrix conforming to the position of the openings 31 above. The openings 31 and the photocells 32 also correspond precisely to the position of sample testing wells 33 of a sample tray 14 which is received in registry above the tray holder 29 when a test is to be conducted. The sample tray 14, or at least the bottom of each well 33, is translucent so that light passing through the diffuser 28 penetrates the wells and their contents, passes through the openings 31 in the tray holder 29 (and usually through a collimator) and reaches the photocells 32 below, which individually sense the intensity of the light passing through each well. The photocells may be of the type manufactured by Clairex Electronics of Mt. Vernon, N.Y. as Model CL702L. This tray holder 29 is preferably of a dark, light-absorbing color such as black to reduce light transmission between the wells and reflection of diffracted light within any one well. The tray holder arrangement assures that all light passing through the openings 31 is from the wells 33 rather than through other areas of the translucent sample tray 14.

The sample tray 14 is preferably a disposable, molded plastic tray, each well of which holds approximately 0.5 milliliter. Trays of this type are commercially available and have been used previously for simple visual type "reading" techniques as discussed above. The wells 33 are often referred to as "microtubes", since they replace cumbersome full-sized test tubes which were used in the past for this type testing.

Figure 3:
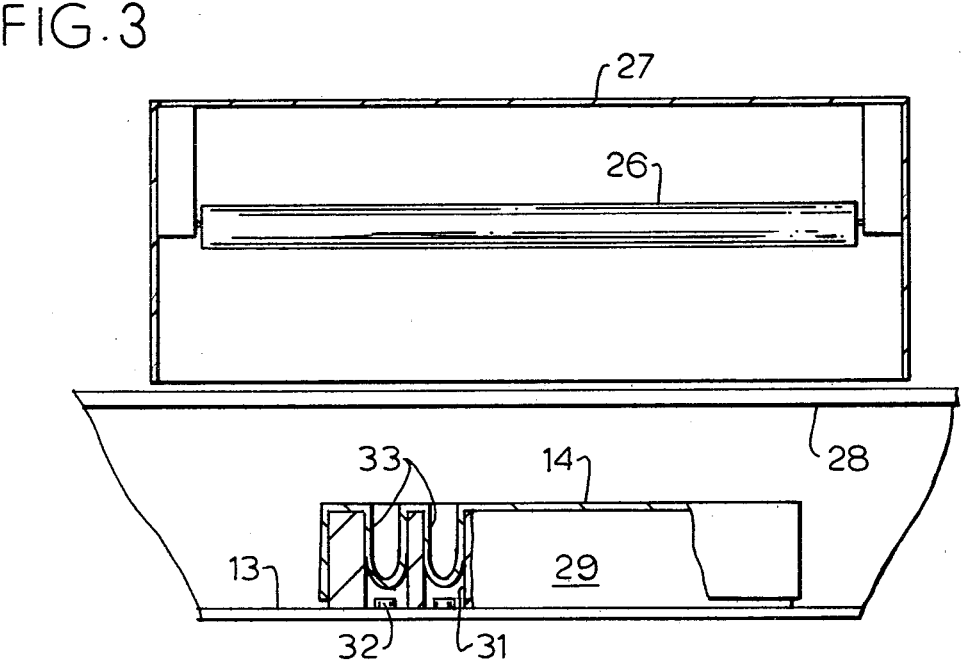
FIG. 3 is a sectional elevational view showing a portion of the apparatus of FIG. 1.

FIG. 3 shows a portion of the internal apparatus of the optical detection unit 11 in cross section. The drawing is somewhat schematic, without details of the structural supporting arrangement within the unit 11 and the drawer 13, but shows the relationship of the lighting components 26, 27 and 28 to one another and to the sample tray 14, the tray holder 29 and the matrix of photocells 32. The bottom of a supporting surface of the drawer 13 is shown in this schematic view, with the photocells 32 mounted on that surface and the tray holder 29 surrounding and extending above the array of photocells 32. The sample tray 14, several wells 33 of which are indicated in FIG. 3 fits snugly over the tray holder 29 with the wells 33 extending down into the openings 31 of the tray holder with little side-to-side tolerance so that registry of the sample wells with the photocells is assured. A collimator may be located below the wells 33.

The light source illustrated is a convenient and preferred form; however, any light source or a plurality of light sources which will provide light of equal intensity directed into each well 33 of the sample tray 14 is sufficient. In this regard, an alternative form of light source and detection system is described below in connection with FIG. 8.

The single diffuse source 26,27,28 need not put out a uniform light. The light need only be roughly even. Also, the photodetectors 32 may be inexpensive ones, providing signals of different strengths for the same light intensity, so long as the invention is practiced with an initial calibration step. In this step, the light source 26,27,28 directs light over all the photodetectors 32 either without a tray 14 positioned above them or with an empty tray 14, to take any variations in the plastic material of the tray into account in the calibration. As another alternative, the tray wells 33 may be filled and then run through before any culture, at zero time relative to growth. In the calibration, a scan is made and all values, i.e. photodetector output signal values, are stored. When each actual test is run, a difference or ratio signal is created for each photocell, so that only the difference in sensed light intensity is used, disregarding effects of localized differences and intensity and differences in the photocells themselves.

Figure 4:
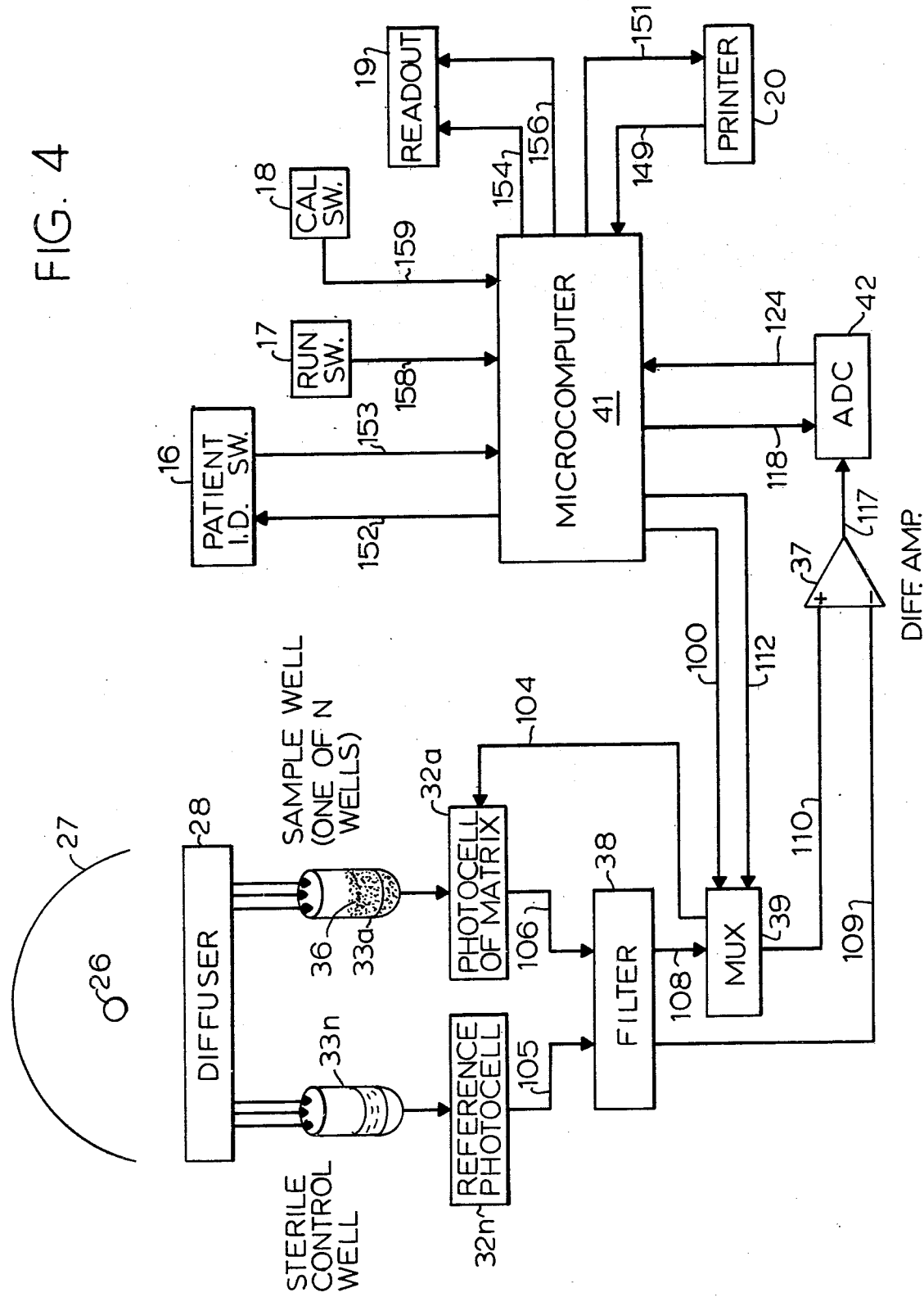
FIG. 4 is a block diagram of the apparatus of FIG. 1 as used for determining minimum inhibitory concentration.

The reference photocell $32n$ is preferably outside the area of the tray, although it may be (as shown in FIG. 4) beneath a sterile or empty well $33n$ of the tray.

As discussed above, the sample tray 14 is preferably laid out in a rectangular matrix, which may comprise for example eight rows and ten columns. Other arrangements would be adequate, but a rectangular matrix is space-efficient and convenient. The wells 33 may, as for obtaining MIC values, contain various dilutions of different antibiotics, and these may be arranged such that each of the ten columns of wells contains a single antibiotic in a series of different dilutions. There may be seven different concentrations of each antibiotic, with the eighth well of at least several of the columns used for control purposes. For example, one control well might be used for unrestricted growth of bacteria, and another well used to represent no growth, with no bacteria inoculated into the well.

Into the wells containing the various dilutions of different antibiotics (for determining MIC values) is introduced the patient bacteria sample borne within a culture medium. This bacteria culture is uniformly inoculated into each well, and this may be accomplished by commercially available devices having a matrix of prongs (not shown) arranged to register with each well to be inoculated in the commercially available sample tray 14. Of course, the antibiotics and the bacteria culture may be introduced to the wells in the reverse order, but for convenience, efficiency and reliability it is preferred that the antibiotic be introduced first.

FIG. 4 indicates diagrammatically the operation of the susceptibility testing apparatus 10. The lamp 26, reflector 27 and diffuser 28 are shown transmitting uniform diffuse light through a sample well 33a of the matrix of wells of the sample tray 14. The well 33a contains one dilution of one of the antibiotics being tested, inoculated with a controlled volume and known concentration of the bacteria in a culture sample. The same uniform diffuse light is also transmitted through a well 33n containing no bacteria for providing a light intensity reading corresponding to zero bacteria growth.

After an incubation period sufficient to allow some detectible growth of the bacteria in the well 33a in the event that growth is not prevented by the particular antibiotic in the particular concentration being tested, a growth culture 36 results therein. The light from the diffuser passes through this culture 36 and through the bottom of the well to a photocell 32a of the photocell matrix. Here the intensity of the light is sensed and converted into an electrical analog value corresponding to the opacity of the culture 36. This opacity value represents the turbidity of the culture, stemming from the net effect of light absorption and scatter in the well 33a. At the same time, the diffuse light passes through the sterile control well 33n to a photocell 32n of the photocell matrix. Again, the sensed light intensity is converted into an electrical analog reference value.

The photocell 32a is connected to a plus input of a differential amplifier 37 through a noise filter 38 and a multiplexer 39 which functions to select each photocell 33 of the matrix of photocells in a prescribed sequence under direction of a microcomputer 41. The sequencing, being automatic, is very fast, going through 80 or 96 wells of a tray 14 in about five seconds or less. The automatic electronic scan has no moving parts—an important feature.

Electronic sequencing is much more reliable than mechanical movement of a tray or other mechanical sequencing. Multiplexing has the advantages of speed, accuracy, reliability and maintainability, i.e. easy maintenance. For at least these reasons, the invention is a significant improvement over mechanical scanning. Thus, the photocell 32a shown in FIG. 4 is connected to the differential amplifier 37 only when the multiplexer 39 momentarily selects that particular photocell. The reference photocell 32n is connected to the minus input of the differential amplifier 37 and provides a reference voltage which is subtracted from the plus input to provide an analog differential output. Thus, the light intensity or turbidity value signal emanating from the differential amplifier 37 is in the form of a reference voltage which varies according to turbidity of the sample being sensed, representing the increase in turbidity of that sample since inoculation. Each analog signal is transmitted in its turn to an analog-to-digital converter 42 which converts the analog to a digital signal and sends it to the microcomputer 41.

The microcomputer 41 (see FIGS. 5 and 6) functions to correlate differential digital values (from the ADC 42) representing, for example, bacterial growth for the various wells with the particular drug and its concentration in the subject well. From such correlation, the microcomputer selects, for example, the zero growth indication stemming from the weakest concentration of each drug, and this concentration becomes the MIC for that particular drug. If none of the wells containing a particular drug indicates inhibition of growth, the microcomputer prints out the fact that the infectious organism is resistant to that particular drug.

The remaining apparatus indicated in FIG. 4 is described below with reference to the other figures.

Figure 5:
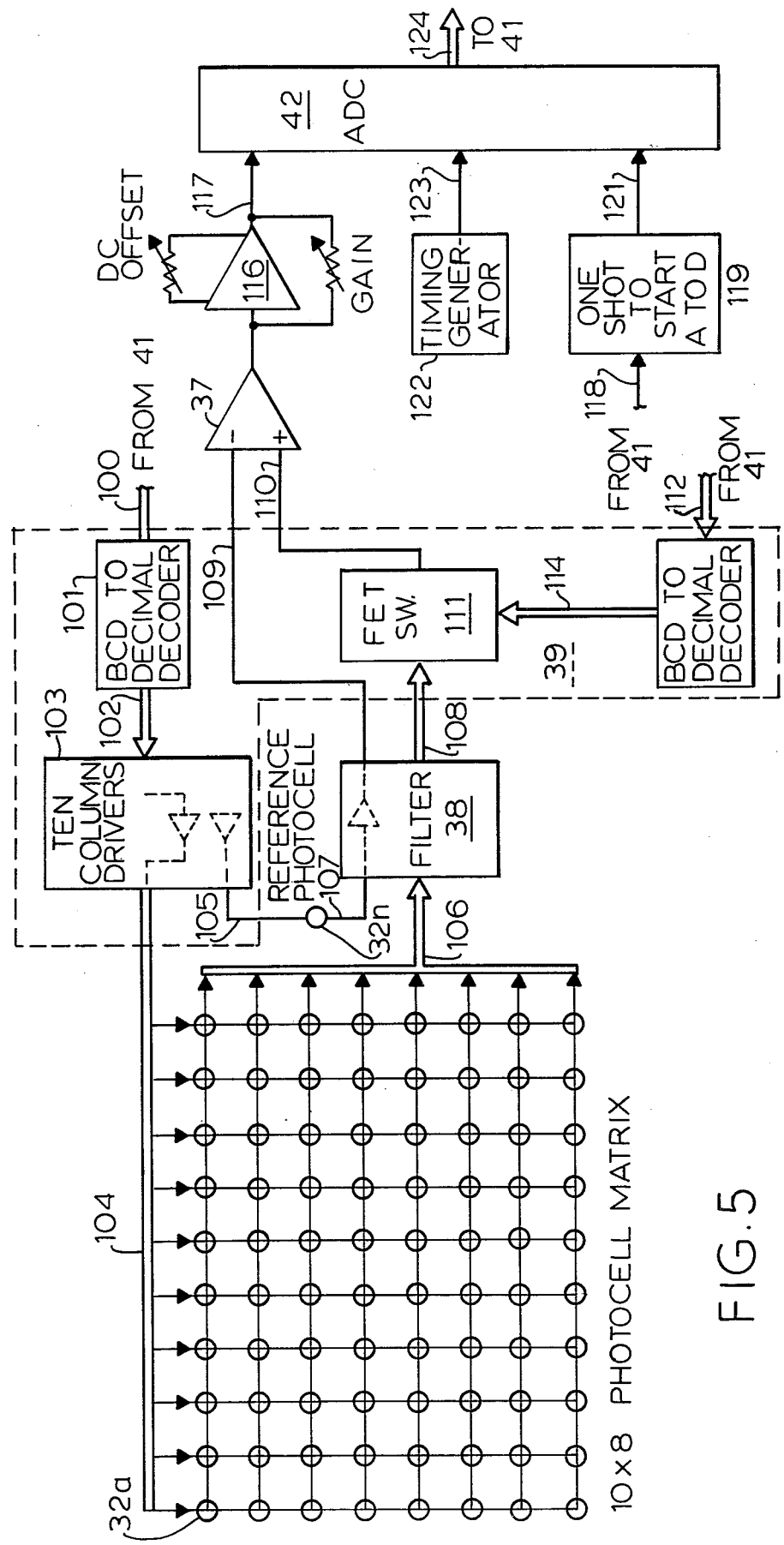
FIG. 5 is a block diagram of an analog-to-digital converter subsystem usable in the apparatus of FIGS. 1–4.
Figure 6:
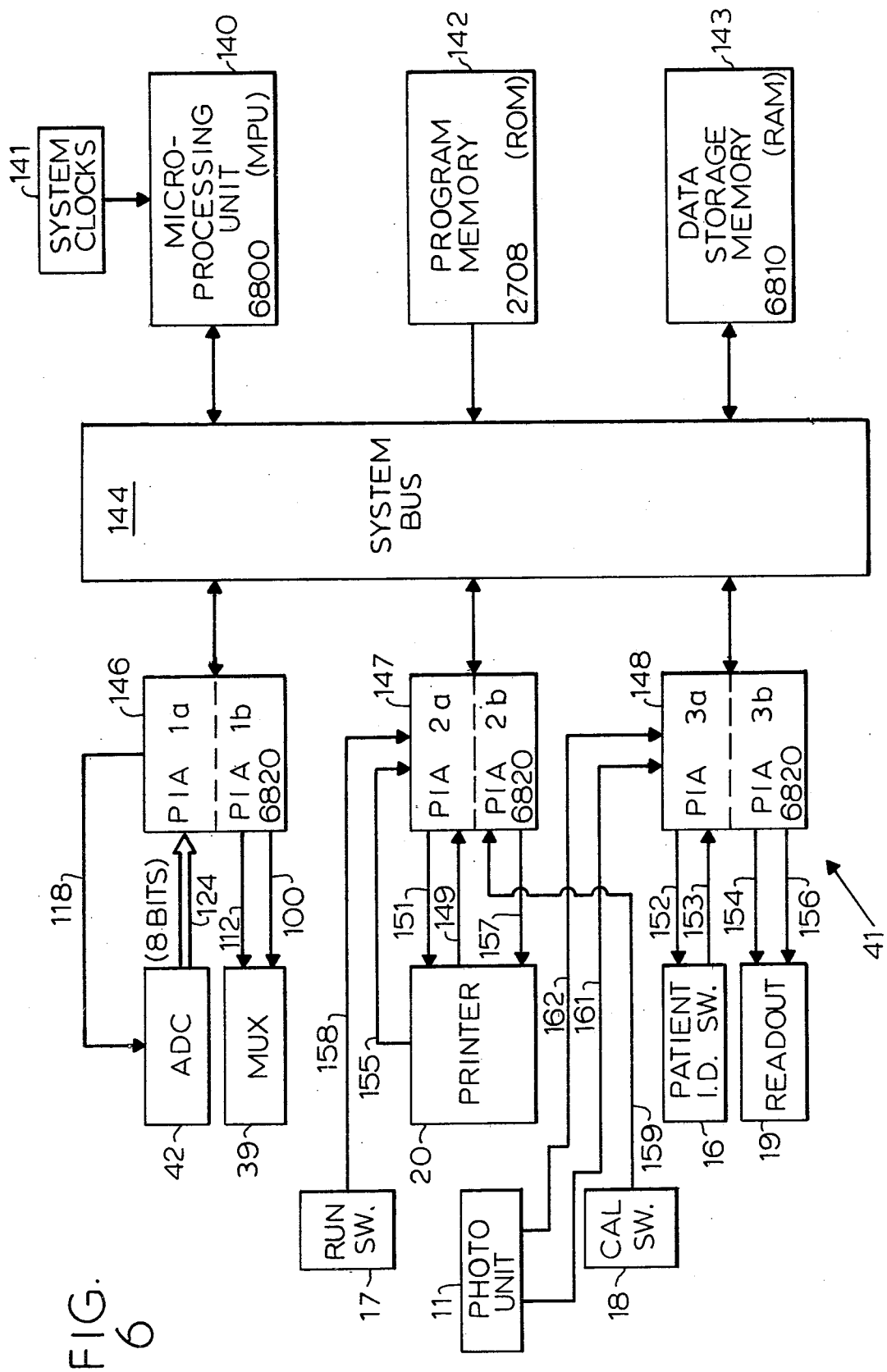
FIG 6 is a block diagram of a microcomputer portion of the apparatus.

The analog circuitry associated with this system 10, including the analog-to-digital converter, is set forth in the detailed block diagram of FIG. 5. FIG. 5 includes the noise filter circuit 38, the multiplexer circuits 39 which are included within the dashed line box, the differential amplifier 37, and the analog-to-digital converter 42 along with its related supporting circuitry. A ten by eight photocell matrix is also shown in FIG. 5 for clarity of understanding of this part of the system 10. A twelve-by-eight system (or other such system) may be used instead.

The multiplexer 39 includes a binary coded decimal (BCD) to decimal decoder 101 driving column drivers 103, and another BCD to decimal decoder 113 controlling FET switches 111. A four bit digital line 100 from the mirocomputer 41 is connected to the binary coded decimal input of the binary coded decimal to decimal decoder circuit 101 (which may be preferably implemented as a type 7442 TTL integrated circuit or equivalent). Ten output lines 102 from the decoder 101 are connected to ten driver circuits 103. The driver circuits are preferably implemented as operational amplifiers type LM 324 or equivalent.

As already explained above, the photocell matrix is arranged as a rectangle with ten columns and eight rows. Thus, the outputs from the ten driver circuits 103 are applied to the ten columns respectively via a bus 104 such that when one driver is excited by operation of the decoder 101, an excitation voltage is provided to one of the column drive lines corresponding to the binary coded decimal column select information input to the decoder 101 via the data line 100 from the microcomputer 41. An eleventh of the drivers 103 applies voltage continuously through a drive line 105 to the reference cell 33n.

Eight row lines 106 and one line 107 from the reference cell 32n are applied as inputs to nine active filer circuits within the filter 38. Each filter circuit is preferably implemented by an operational amplifier, type LM 324 or equivalent. The filters 38 function to remove power line ripple so that the eight row output lines 108 and a reference output line 109 carry DC voltage levels only. The eight output lines 108 are applied to eight field effect transistor switches 111, respectively. The switches are preferably implemented as integrated circuits type CD4016 CMOS quad bilateral switch gate chips or equivalent. An output line 110 from the switches 111 is connected directly to the plus input of the differential amplifier 37. The ninth line 109 is applied directly to the minus input of the logarithmic differential amplifier 37.

A three bit digital line 112 from the microcomputer 41 is connected to the input of a second binary coded decimal to decimal decoder 113 which is also preferably implemented as a type 7442 TTL integrated circuit or equivalent. The decoder 113 functions to select one of eight output control lines 114 which in turn select one of the eight field effect transistor switches 111 to connect one of the filtered row lines to the plus input of the logarithmic differential amplifier 37, in accordance with digital row select information received from the microcomputer 41.

The logarithmic differential amplifier 37 is preferably implemented as an Analog Devices type 757 or equivalent, and the purpose of the amplifier 37 is to correct for variations in light intensity from the light source 26. The light-variation-corrected analog voltage output from the amplifier 37 is supplied as an input to an operational amplifier 116 which is provided with external potentiometers to control gain and DC offset of the incoming signal from the amplifier 37.

An output line 117 from the amplifier 116 is supplied as an analog input to the analog-to-digital converter 42 which is preferably implemented with a National Semiconductor MM5357 integrated circuit or equivalent. A digital control line 118 from the microcomputer 41 is connected as a trigger input to a monostable multivibrator one shot 119, preferably implemented as a type 74121 TTL integrated circuit or the equivalent. An output pulse from the one shot 119 of appropriate amplitude and duration is supplied via a line 121 to the analog-to-digital converter 42 to start the conversion process. A timing generator (e.g. type 555) 122 applies timing pulses via a line 123 to the analog-to-digital converter 42 to control the sequence of operations thereof. The analog-to-digital converter 42 utilizes the timing pulses supplied on the line 123 during a conversion cycle to digitize the analog information on the line 117 and provide an eight bit digital output via an eight bit output bus 124 which is supplied to an input port of the microcomputer 41.

The microcomputer 41 forms the central portion of the system 10. The microcomputer includes a single chip monolithic microprocessing unit (MPU) 140, which is preferably implemented as a type 6800 manufactured by Motorola Semiconductor, American Microsystems, and other suppliers. Although this particular microprocessor was chosen for the described preferred embodiment of the present invention, other types of microprocessors would function equally as well, for example the Intel 8080, the Mostec 6502, the Zilog Z80, The Fairchild F-8, etc. A suitable two-phase clock 141 provides the necessary clock signals to the microprocessing unit 140.

A main system program like that which is set forth in hexadecimal code in the table following the specification of the present invention may be loaded into one and a half kilobytes of programmable read only memory 142. The read only memory 142 is preferably implemented with 2708 programmable read only memories produced by Intel and other suppliers. Other PROMs would be well suited for the program memory 142. The microcomputer 41 also includes one kilobyte of random access memory (RAM) 143 which provides volatile storage of data to be processed as well as a stack for the microprocessing unit 140. The microprocessing unit 140, the clock 141 through the microprocessing unit 140, the program memory 142 and the data storage memory 143 are connected in parallel to the system bus 144 which includes an eight bit data bus, an eight bit control bus, and a sixteen bit address bus.

Input output interface is accomplished with three peripheral interface adapters (PIA) 146, 147 and 148 which are connected to the system bus 144. The interface adapters 146, 147 and 148 are preferably implemented as type 6820 integrated circuits produced by Motorola Semiconductor, American Microsystems, and other suppliers. These integrated circuits contain two ports apiece. Each port may be used either to input data to the microprocessing unit 140 or to output data to output devices, as will be explained hereinafter.

The first interface adapter 146 has its first port connected to receive the eight bit digitized information via the bus 124 from the analog-to-digital converter 42, as shown in FIG. 5. The first port of the interface adapter 146 also provides the control signal line 118 which is connected to the one shot 119 which functions to start the analog-to-digital conversion process of the converter 42. The line 118 will be further explained hereinafter. The second port of the interface adapter 146 is connected to the multiplexer 39 with four bits provided for the column select control signal via the bus 100, and the three remaining bits provide for the row select control signal via the bus 112.

The second peripheral interface adapter 147 includes a first port which controls the printer 20. Two bits of data are input from status indicators in the printer 20 via a line 149. One of these bit positions is from a microswitch which indicates that the paper form has been properly inserted and that a printout can be made. The other bit is a signal from the printer electronics which indicates that the printer is either in a "print" or a "wait" operational mode. Four bits of the first port of the interface adapter 147 are also used to control the printer and shift data to be printed into the printer 20. The data is entered serially via a line 151 from the first port of the adapter 147 to the printer 20. Other control functions carried out by the four bits on the line 151 include line feed (advance the paper one line), print (cause the print solenoid to make an impression on the paper), and shift (move the next data bit into position for printing). The second port of the interface adapter 147 is not used in the present embodiment.

The third peripheral interface adapter 148 includes a first port which reads the thumbwheel switch 16 for patient identification information via a four bit line 153. The upper four bit positions of this first port of the adapter 148 are used to select and enable one of the four thumbwheel positions via a four bit line 152. One bit position of the line 152 is low to enable one of the four switching positions. The lower four bits of the first port of the adapter 148 are used to read data via a bus 153 from the switch position selected by the upper four bits. The data from the switch represent a binary number between zero and nine. The second port of the interface adapter 148 is used to supply data to the alpha-numeric display readout 19. The display 19 is the Burroughs model SSD0132-0070 self-scan display unit with built-in electronics. As explained, it is controlled via a line 154 from the second port of the third peripheral interface adapter 148. Data to be displayed on the display 19 are entered into the unit via a line 156 in a six bit code for all alpha-numeric characters as well as some special symbols. The data are read in from left to right and appear on the display until new data are entered. Thus, the upper two bits are provided via the line 154 to control the display, with one of the bits being a clear line and the other being an enable line. The lower six bits are provided via the line 156 for the purpose of sending parallel data to the display presented to the user in accordance with the operation of the system 10.

In addition to the characteristics of the interface adapters 146, 147 and 148 described hereinabove, each adapter also has an interrupt function. The interrupt is an additional line which is available for monitoring the status of external devices. In the presently described system 10, the interrupts are used to monitor operator actions of several types. Interrupt capability which results in an output rather than an input is termed a strobe. Strobes are utilized in the system 10 as well as interrupts. Thus, the first peripheral interface adapter 146 controls the conversion of data from analog-to-digital format via the analog-to-digital converter 42 by utilizing a strobe line 118 which is connected to the one shot 119 (FIG. 5) to start the analog-to-digital conversion operation.

The second peripheral interface adapter utilizes an interrupt from the printer 20 via a line 155 and utilizes one interrupt each from the run switch 17 via a line 158 and calibrate switch 18 via a line 159. The second port of the second adapter 147 utilizes the output strobes via a line 157 to cause the printer 20 execute a print cycle.

A third peripheral interface adapter 148 has two interrupt inputs: one from a microswitch indicating that the photo unit drawer is open via a line 161 and one indicating that the drawer is closed via a line 162.

The printer 20 may be implemented as an MFE model TK11E or Practical Automation DMPT-9, both with electronics package. Data is fed from the microcomputer 41 via the line 151 which generates the proper control signals to enable the printer electronics to cause the printer 20 to print, line feed or shift data into internal registers. The data is fed to the printer 20 in serial format, stored in buffers in the printer electronics, and is then printed in parallel. The command to print is generated as a strobe output of the second port of the second peripheral interface adapted 147 via the line 157. The printer is a commercially available unit presently being sold for the original equipment manufacturer (OEM) market.

Determining minimum inhibitory concentration (MIC) (FIG. 7)

One method using the system 10 is explicated by the flow chart set forth in FIG. 7. Therein, at a power on step 166, the operator turns the power on to the system 10. At that point, the display 19 informs the operator to insert the calibration tray. At insertion step 168, the operator inserts the tray, and at step 169, the operator closes the drawer. At a logical step 170, the system checks the identification of the tray in the drawer. For this purpose a binary code may be implemented using the uppermost right two wells of the tray, either of these wells being either opaque or transparent, thus providing identification of four possible types of trays. This code is made to correspond to the combination antibiotics which the tray contains.

In the event that the type of tray is not identified at step 171, the system asks whether the tray is inserted backwards at step 172. If so, the readout 19 displays a tray backwards indication at step 173, and the operator opens the drawer at a step 174 and removes the tray, orients it correctly, and reinserts it, then repeats steps 168, 169, 170 and 171.

Once the tray is identified at step 171, the readout 19 displays the tray type at step 175, and directs the operator to press the calibration switch 18 at a step 176. At step 177, the operator presses the calibration switch 18 whereupon the system tells the operator to wait at step 178. The wait signal remains until the system informs the operator to remove the tray at step 179. The operator opens the drawer at step 180. In the event that the tray is not in backwards, and yet the tray remains unidentified at step 181, the operator is then instructed to open the drawer to manually inspect the tray to find out why the system 10 is unable to identify it.

At step 182, the readout 19 tells the operator to close the drawer, and at step 183 the operator removes the tray and closes the drawer. The readout 19 then tells the operator that if a next test is desired, he should press the run or calibrate button at step 184. At a step 185, the operator actually presses the run or the calibrate switch. If the system has been previously calibrated at step 186, then the readout 19 directs the operator to insert the test tray at step 187. However, if the system 10 has not been calibrated at step 186, the program returns to step 167 and the calibration procedure is carried out as set forth in steps 167 through 185.

At step 188, the operator opens the drawer and inserts the test tray. The display 19 then tells the operator to close the drawer at step 189. The operator closes the drawer at step 190 and the tray identification is determined at step 191. In the event that the tray is not identified, the system then determines whether the tray is in backwards at step 192. If so, the system informs the operator that the tray is in backwards by a readout display at step 193. In the event that the tray remains unidentified and it is not in backwards, then at step 194, the operator is informed that the tray is unidentified and the program loops back to step 180 whereupon the operator opens the drawer and repeats steps 180 through 191.

Once the identification of the tray has been determined at logical step 191, the system 10 displays the type of tray at the readout with step 195. Then the operator is informed to set the patient identification information into the identification switch 16 and insert the form to be printed into the printer 20 at step 196. The operator performs these operations at step 197 and when they are completed, the display 19 tells the operator to press the run switch 17 at step 198. The operator presses the run switch 17 at step 199 and the patient identification information is displayed at step 200. Then, the patient identification is printed on the form at a step 201 and then the MIC values and interpretive information are printed on the form in step 202 to produce the form 203.

Once the form is printed with the patient identification MIC values and interpretive information the display tells the operator to remove the tray at step 204. The operator opens the drawer and actually removes the tray at step 205 whereupon the display 19 tells the operator to close the drawer at step 206. The operator closes the drawer at step 207 and the apparatus 10 then instructs the operator to perform the next operation of either "run" or "calibrate" at step 208 whereupon the program loops back to step 185 where the run or calibration switches are operated and the program is repeated as heretofore described until all of the samples have been evaluated by the system 10.

Comparisons to reduce errors due to the tray and to light intensity and photodetector differences:

It will be apparent that the tray 14 itself might be a source of error. That is, its own light transmissivity and opaqueness and flaws can substantially affect the light transmissivities received by the photocells 32, in addition to the light transmissivity of the liquid in the wells. The trays 14 can vary from tray to tray, and they can also vary in a tray from well to well. This could, of course, lead to substantial errors that would give false impressions and false results if not compensated or corrected.

The present invention accomplishes the needed correction by two different types of comparison stages.

Figure 13:
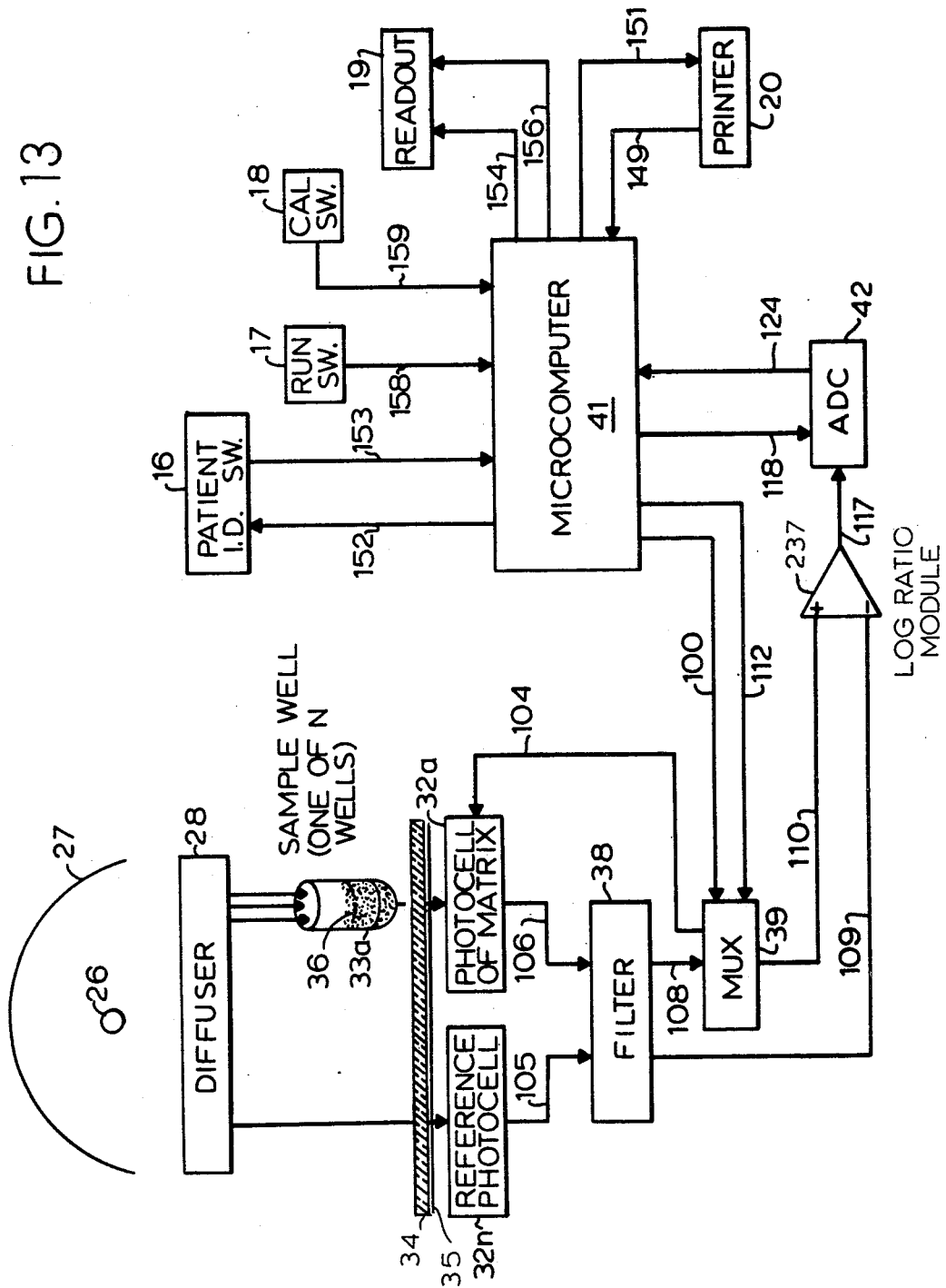
FIG. 13 is a block diagram of the apparatus of FIG. 12.

First, for each reading in any sequence of wells 33 in the tray 14, each well 33 is immediately compared with the value obtained by direct light transmission to the reference photocell 32n. While this may be done through a sterile control well, as shown in FIG. 4, it is preferably done directly, completely outside the tray 14, as shown in FIGS. 10 and 13, with the light to the reference photocell not passing through any portion of the tray. From this comparison, the device provides an after culture value for each well, which is a function of the after culture signal values (or amplification thereof) for the tested well and for the reference photocell. This, of course, represents a comparison of the light received at each photocell in the main array and the intensity of the light received at the reference photocell. The signal may be amplified and is used as the operative signal, as shown in FIG. 4. The after culture value for each well may be called a "difference" signal value, regardless of the type of function which is used in comparing the two values (test well vs. reference photocell) to produce this value. In the embodiment of FIG. 4 the subtractive difference preferably is taken between the two values, and the differential amplifier 37 amplifies the difference signal. However, the signal value produced in the embodiment of FIGS. 10 and 13 is a ratio, and the signal from each well is compared with the reference photocell signal by means of a log ratio module 237. In other words, there is again a "difference" signal, but it is a difference in logarithms, so that the subtraction is really a division, and a quotient or ratio is obtained instead of a difference expressed as a logarithm.

Thus, in the invention, each reading of each well, at each stage where readings are taken, is compared by a first comparator means with the reading at the reference photocell, and a difference or ratio signal developed from it. By this procedure, variations in light intensity from the source over time, as would be induced by supply voltage fluctuations, have no effect on the readings. Such variations will vary the reference and well photocells proportionately, so that a ratio will cancel the errors out. This is the purpose of the reference photocell.

Second, to further reduce the possibility of error particularly due to flaws in the tray, and in view of the fact that each tray 14 is positively identified in the apparatus, as has already been described, a prior reading may be taken through the tray before the reading after bacterial culture; this prior reading is stored and is later compared with the sample reading.

One way of taking the prior reading is to take a reading of the tray 14 in its empty state, before it is filled with fluid, to compare the reading through each empty well with the reading of the reference photocell, as above, and to store the resulting difference signal or ratio signal in the data storage portion of the microcomputer 41. Then the ratio signal (or difference signal) derived from the liquid at the time of the after culture reading is compared with the ratio signal (or difference signal) of the empty wells. Thereby, each well is compared with itself when full and when empty, and errors due to the wells are substantially eliminated.

Another way of taking this prior reading is to take the prior reading, not of the empty tray but of the tray just after its wells have been filled with the solution and prior to the culture; in other words, at substantially zero time so far as growth or culture is concerned. This means that the reading is taken through the actual solution, and the ratio of that reading to the reference electrode is stored in the data storage bank for the later use.

With the zero based signal (however obtained) in the data bank, and with the ratio or difference signal provided for each well for the liquid after culture, then, before proceeding further, the next step is to compare by a second comparator means the two ratio (or difference) values, that is, to compare the ratio of the signal derived from the light transmissivity of the specimen after culture to the direct light reception by the reference cell, with the ratio of the empty tray or tray with the same liquid at zero time to the signal from the reference cell. This second comparison may also be made by calculating a ratio of the two ratios, which is preferably accomplished by taking the difference in logarithms of the two ratios, resulting in another logarithm which is the log of the comparison ratio, or of what may be called the comparison signal.

In the next step, a third comparison depends upon what test is being run. Basically, it is a comparison of the ratio signal obtained from the second comparator means, which preferably is the logarithm of the comparison signal, with values that are stored in the data storage means to determine the final asked-for result.

For good results in this last step, especially when applied to MIC procedure, a distinction is made between a growth state and a no-growth state. The instrument determines at the output from the second comparator means, a voltage level or logarithm value that represents the extent of bacterial growth, when that voltage level is compared to voltages that are obtained from known sterile and growth controls, these voltage values being stored in the data bank of the microcomputer 41. A first step here is to determine whether there is an adequate voltage (logarithm value) difference between the readings obtained from the sterile and the growth control wells. This is done preferably by comparing the ratios for the two wells, i.e. the products of the first comparator means for the two wells, which are logarithms of ratios of well readings vs. reference readings. The comparison of the two control values is done by taking a difference between the two logarithms. The resulting difference is compared to a predetermined, stored value representing adequate growth-sterile difference for the test. If there is an inadequate difference, this means either one of two things, either that there had not been sufficient growth to provide an adequate difference, or that the sterile well had been contaminated and that there had been growth there. In either case, the instrument will display a reading such as "insufficient growth-sterile difference", and the computer returns to the beginning of the program. The operator then checks to see which of these two possibilities is the one that is present. If there is insufficient growth, it may be due to a lack of time or because there was nothing to grow. If there were contamination, that would show and be readily detectable, and the test must be re-done.

Once the computer has established that there is an adequate difference between the sterile condition and the expected growth condition from one well to another, the calculated logarithm values and their difference are used for computation of a break point, or a limit comparison signal value. Preferably, the break point is biased toward the sterile value to achieve more sensitivity to growth detection, via a preselected fraction of the sterile-growth logarithm difference. The break point may, for example, be placed at 25% of the determined sterile-growth difference (preferably a logarithm value as above), added to the log value for sterility. For all wells where there has been less growth than that represented by 25% of the determined growth-sterile difference for the test being conducted, then the concentration of those wells is considered as inhibitory. For each drug being tested, the concentration closest to the break point, but on the inhibitory side, is selected as the minimum inhibitory concentration value. Thus, supposing that there are a series of wells of different dilutions and that the operation is moving from wells of greater growth towards those of lesser growth and toward the sterile condition, then the minimum inhibitory concentration is not found until the first well is reached which shows less than 25% of the determined difference between the sterile and growth control wells. In this way, a "floating threshold" is utilized, i.e. one which is calculated from controls in the very test being conducted and with the same organism being tested, rather than a fixed threshold which has been calculated based on prior information and stored.

Another important comparison which should be performed preferably at least once a day, before series of tests are performed, is an initial calibration step. This initial calibration is in lieu of the empty tray (or just filled tray) reading procedure described above. Like that procedure, this calibration procedure is important in that it enables the use of a light source which is not totally uniform for each photodetector, but only generally uniform, and also the use of inexpensive photodetectors which may not be uniform or totally constant, over a long period of time, in their sensitivity. By this procedure the light is first passed directly (no tray) to all photodetectors, including the reference photocell, and ratio readings (preferably their logarithms) are taken as above and recorded. These values are stored and give a relative base line or initial calibration value for each photocell. All subsequent after culture values (which are preferably logarithms of ratios as above) are compared to these base line readings, and expressed as "difference" (or log ratio) readings. Thus, any differences in sensitivities of the various photocells, or differences in light intensity due to position, are "zeroed out" by comparison of after culture ratios with initial calibration ratios, the comparisons being separate for each well.

Figures 8, 9:
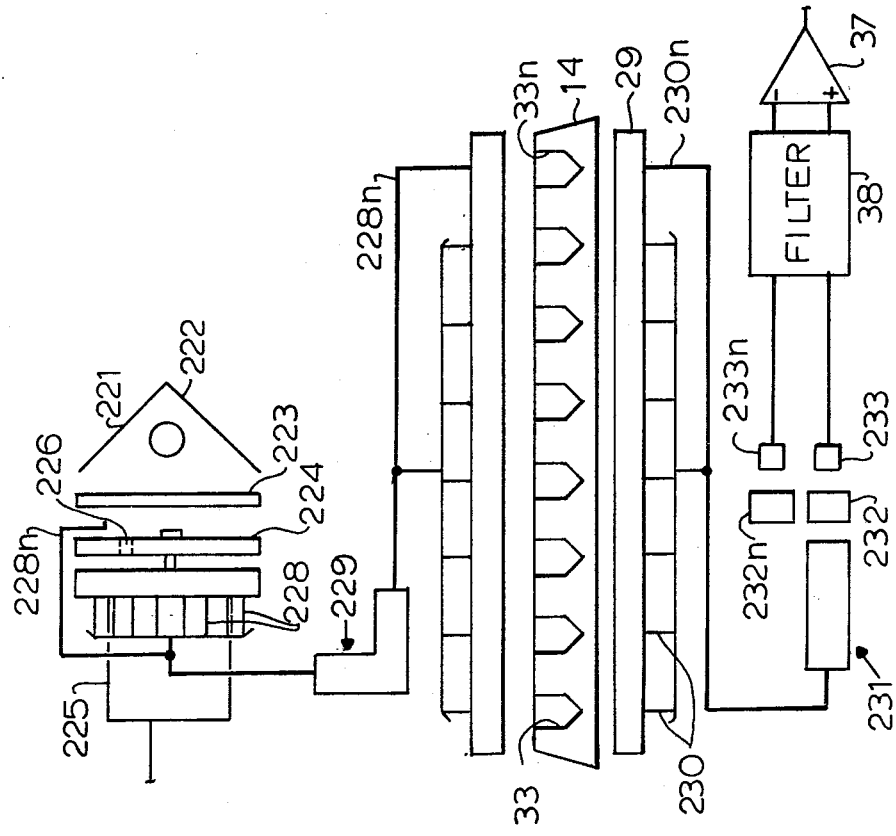
FIG. 8 is a schematic elevation view showing an alternative form of optical detection apparatus which may be included in the apparatus of the invention.
FIG. 9 shows a form of printout which may be utilized in connection with the apparatus of the invention when determining minimum inhibitory concentration.

An alternate type of light source (FIG. 8)

FIG. 8 shows schematically an alternative arrangement for passing light through the wells 33 of the sample tray 14 and detecting the resultant light intensity passing through each well. The apparatus of FIG. 8, which utilizes fiber optics to transmit light, would replace the form of light source and diffuser 26, 27 and 28 shown in FIGS. 2, 3 and 4. It would also eliminate the need for a large plurality of photocells 32 in a matrix as shown in FIG. 2, and would replace the multiplexing unit 39 (FIG. 4) with a substitute arrangement which selects one cell at a time for receipt of a penetrating quantum of light.

The apparatus of FIG. 8 includes a light source 221 and a reflector 222, directing light through a lens 223 toward a rotatable selector plate 224 driven by a stepper motor 225. The selector plate 224 has a single opening 226 (dashed lines) which sequentially directs light to different fiber optic fibers 228 of a fiber optic bundle 229. The stepper motor 225 is under the control of the microcomputer 41 via the lines 100 and 112 (FIGS. 4 and 6), in lieu of and to perform the same function as the multiplexer 39 indicated in FIGS. 4 and 6. The fiber optic fibers 228 of the bundle 229 each go to individual testing wells 33 of the tray 14. The fibers are indicated only schematically, as is the bundle 229.

Below the wells 33 are a second plurality of fiber optic fibers 230 of a second bundle 231. Transmitted light from each well is collected by a fiber 230 of the bundle 231 and fed via a lens 232 to a single photocell detector 233. A value corresponding to the intensity of incident light is then fed to the filter 38, then to the plus input of the differential amplifier 37, as in the apparatus of the other embodiment described above.

In order to provide a control or reference value which may be fed into the minus input of the differential amplifier 37 to represent a base light intensity corresponding to zero bacterial growth, there must be an optical fiber which always carries light through a reference sterile control well, i.e. the well 33n of FIG. 4, also indicated in the schematic representation of FIG. 8. Accordingly, a single optical fiber 228n is positioned at the lens 223 in such a way that it receives and carries light continuously whenever the lamp 221 is energized, i.e. whenever any of the wells 33 is being tested. The fiber 228n extends to a position adjacent to the sterile control well 33n as shown, and a receiving fiber 230n carries the transmitted light to second lens 232n. The resultant analog light intensity value for the control well is fed through the filter 38 to the minus input of the differential amplifier 37, so that the differential amplifier yields a differential analog signal corresponding to increased turbidity in the tested well from bacterial growth.

The remainder of the system remains the same as described above. The principal advantage of the form illustrated in FIG. 8 is the use of a single light source focused on the fiber optic bundle and a single detector for all test wells of the sample tray, providing a more uniform measurement over the matrix of test wells in the tray. Light is transmitted through only two wells of the tray at any given time: the well currently being tested for turbidity, and the sterile reference well 33n.

The subsystem of FIG. 8 allows for close standardization and easy calibration and checking.

A printout ticket for MIC (FIG. 9)

FIG. 9 shows a form of printout ticket 24 which may be used in conjunction with the present invention, with exemplary MIC susceptibility information and therapy information. As discussed above, the apparatus of the invention provides a graphic interpretive printout to guide the physician's therapy, an example of this type information being located in the right column of the ticket 24. The computer algorithm translates the MIC values (left column) to dosage ranges that would be necessary to achieve blood levels of each antimicrobic drug to effectively inhibit growth of the organism. FIG. 9 indicates one form that the "therapy guide" information may take. With this format, "−" indicates that the organism tested is resistant to that particular antimicrobic, and that no dosage of the antimicrobic can affect the organism. "+" indicates resistance but that the organism may respond to high intra-muscular intravenous doses. "++" indicates that the organism is intermediate in sensitivity to the particular antimicrobic, and may respond to higher than recommended dose. A printout of "+++" indicates sensitivity to the usual recommended doses of the antibiotic, and "++++" means that the organism exhibits a high degree of sensitivity and thus is an optimum drug with which to treat the infectious organism. A printout of "****" tells the physician that a dosage of that particular antibiotic necessary for therapy may be toxic to the patient.

A modified form of apparatus (FIG. 10)

FIG. 10 is much like FIG. 4, and the same reference numerals are used where the device is unchanged. The differences will be noted.

In FIG. 10, there is no sterile control well; the light from the diffuser 28 passes directly to the reference photocell 32n through a collimator 34, used with all the wells also. This provides a reference signal which can be used as described above in the discussion concerning comparisons which reduce errors.

The differential amplifier 37 is replaced by a log ratio module 237. Thus, the "difference" is made into a quotient, giving more sensitivity.

Otherwise, the apparatus is the same as has been already described.

A variation in the tray holding and drawer arrangement

Figure 11:
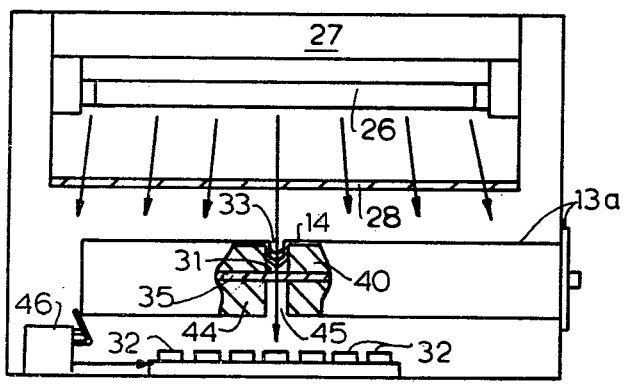
FIG. 11 is a schematic sectional view similar to FIG. 3, showing an alternate arrangement for the test drawer and the manner in which the photocells are positioned, and also indicating use of an optical filter as called for in the embodiment of FIGS. 12–14.

FIG. 11 is supplementary and in some respects alternative to FIG. 3 in showing a preferred arrangement for the light source, the sample tray, and the means of holding the sample tray and collimating the light through the wells to the photocells. A partially broken-away, schematic sectional view in FIG. 11 shows the lamp or bulb 26 with the reflector 27 above and the diffuser 28 below. The drawer arrangement is somewhat different from FIG. 3, with a drawer 13a that slides in and out of the apparatus 10 above and independently of the array of photocells 32. As indicated, the photocells 32 are mounted fixedly below the drawer 13a and of course positioned to receive light passing through each well 33 when the drawer is fully inserted, in the testing position.

The tray 14 rests on a tray block 40 secured within the drawer 13a and having a matrix of openings 31 similar to those described in reference to FIG. 3, for receiving the depending sample wells 33. Below the tray block 40 is a drawer plate 44, also bored at each location of a well as indicated, the drawer plate bores 45 being directly in registry with the openings 31 above. The drawer plate 44 with its bores 45 serves as the collimator 34 discussed in connection with FIG. 10 and also, below, with reference to the embodiment of FIGS. 12 to 14.

As indicated in FIG. 11, there is a space left between the tray block 40 and the drawer plate 44 for an optical filter 35, as discussed below with reference to FIGS. 12 and 13. The filter 35 preferably is slidably received between the two drawer-attached components 40 and 44 above and below, and different filters can be used, as discussed below.

Another feature illustrated in FIG. 11 is the use of a microswitch 46 which is tripped by the back end of the drawer 13a as it is fully inserted into the testing position. This starts the test automatically, and the testing cycle proceeds to completion.

Figure 12:
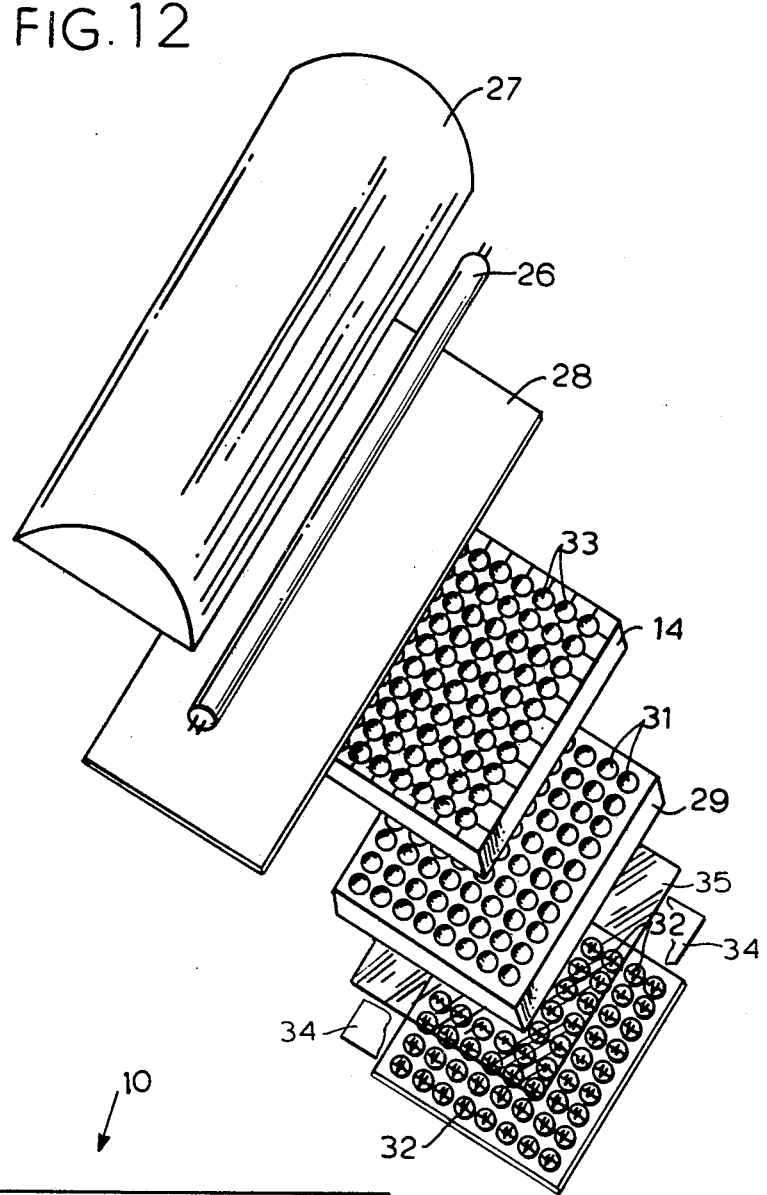
FIG. 12 is a view similar to FIG. 2 of a modified form of apparatus embodying the principles of the invention.

Another modified form of apparatus (FIGS. 12-14)

FIGS. 12 and 13 are quite like FIGS. 2 and 4 except that the collimator 34 is shown and the optical filter 35 is placed between the sample tray 14 and the photocells 32, as also shown in FIG. 11. The exact filter 35 used depends on the test concerned. The filter 35 is made to be easily removable and replaceable. For example, a large number of tests may be run using only three filters one at a time; these three being (for example) filters numbers 809, 863, and 878, of Edmund Scientific Co., 785 Edscorp Building, Barrington, N.J. 08007. FIG. 14 shows the spectral absorber responses of these three filters, 809 at A, 863 at B, and 878 at C.

FIG. 12 shows use of a log ratio module 237, as in FIG. 10.

Use of the apparatus of FIGS. 12-14 in bacterial identification

As discussed above, the sample tray 14 is preferably laid out in a rectangular matrix, which may comprise, for example, eight rows and ten columns. Other arrangements would be adequate, but a rectangular matrix is space-efficient and convenient. In this method, the wells 33 contain various reagents.

Into the wells containing the various reagents is introduced the patient bacteria sample borne within a culture medium. This bacteria culture is uniformly inoculated into each well, and this may be accomplished by commercially available devices having a matrix of prongs (not shown) arranged to register with each well to be inoculated in the commercially available sample tray 14. Of course, the reagents and the bacteria culture may be introduced to the wells in the reverse order, but for convenience, efficiency and reliability it is preferred that the reagents be introduced first.

FIG. 13 indicates diagrammatically the operation. The lamp 26, reflector 27, and diffuser 28 are shown transmitting uniform diffuse light through a sample well 33a of the matrix of wells of the sample tray 14. The well 33a contains one reagent, or group of reagents, and one sensor (e.g., one reagent and one pH indicator), inoculated with a controlled volume and known concentration of the microorganisms in a culture sample. The same uniform diffuse light is also directly transmitted through a filter 35 to a reference photocell 32n.

After an incubation period sufficient to allow some detectable reaction of the microorganism with the reagent in the well 33a, in the event that there is a reaction, a reaction product 36 results therein. The light from the diffuser passes through this reaction product 36 and through the bottom of the well and through the filter 35 to a photocell 32a of the photocell matrix. Here the intensity of the light is sensed and converted into an electrical analog value corresponding to the opacity of the reaction product 36. This opacity value represents the intensity of color of the culture and its reaction with the reagent, stemming from the net effect of light absorption and scatter in the well 33a. At the same time, the diffuse light passes to a photocell 32n of the photocell matrix. Again, the sensed light intensity is converted into an electrical analog reference value.

The photocell 32a is connected to a plus input of a log ratio module 37 through a noise filter 38 and a multiplexer 39 which functions to select each photocell 33 of the matrix of photocells in a prescribed sequence under direction of a microcomputer 41. Thus, the photocell 32a shown in FIG. 4 is connected to the log ratio module 37 only when the multiplexer 39 momentarily selects that particular photocell. The reference photocell 32n is connected to the minus input of the log ratio module 37 and provides a reference voltage which is subtracted from the plus input to provide an analog differential output. Thus, the light intensity signal emanating from the log ratio module 37 is in the form of a reference voltage which varies according to the opacity of the sample being sensed, representing the increase in opacity of that sample since inoculation. Each analog signal is transmitted in its turn to an analog-to-digital converter 42 which converts the analog to a digital signal and sends it to the microcomputer 41.

The microcomputer 41 functions to correlate differential digital values (from the ADC 42) representing bacterial reaction with the reagent for the various wells.

The analog circuitry associated with the system of FIG. 13 includes the noise filter circuit 38, the multiplexer circuits 39 which are included within the dashed-line box, the log ratio module 237, and the analog-to-digital converter 42 along with its related supporting circuitry, all as described before in connection with FIGS. 1-6.

The logarithmic log ratio module 237 is preferably implemented as an Analog Devices type 756 or equivalent, and the purpose of the log ratio module 37 is to correct for variations in light intensity from the light source 26. The light-variation-corrected analog voltage output from the log ratio module 37 is supplied as an output line 117.

Example of bacteria identification

Bacteria that must be identified in the clinical laboratory may be taken from a large number of body sites. Wounds suspected of being infected, nose and throat cultures, aspirates from abscesses, feces, and sputum specimens are some of the more common sites from which bacteria may be cultured. Normally sterile body fluids are also frequently investigated for the presence of bacteria. In suspected cases of septicemia, blood may be sent to the laboratory, and urine is frequently cultured for the diagnosis of urinary tract infections. Additionally, cerebrospinal fluid for suspected meningitis, pleural fluid for suspected pleuritis, pericardial fluid for pericarditis, and ascitic fluid for suspected peritonitis may be sent to the laboratory for the culture, identification, and susceptibility testing of bacteria.

A nurse, physician, or technologist may obtain cultures by either using cotton swabs, or directly inoculating the specimen into a liquid medium. In the case of a liquid specimen, such as blood or a body fluid, the original material is introduced into a bottle or tube of sterile nutrient broth media. For cultures of solid structures, such as a wound, skin, eye, etc., it is necessary to collect a specimen with a swab. Once transported to the laboratory, the swab is streaked over the surface of nutrient agar. Agar is a seaweed derivative that forms a gel. Molten agar may be poured into a shallow, cylindrical glass dish (Petri dish) to form a layer approximately five millimeters deep. When bacteria grow on the surface of the agar, individual organisms which are originally invisible to the naked eye multiply to become colonies that are easily visible. Each isolated colony is the aggregate "off-spring" of a single bacterial progenitor. Thus, by utilizing a single colony or a group of similar colonies, a pure culture of bacteria may be obtained for susceptibility testing or identification. In the case of bacteria that were originally isolated in a liquid nutrient broth, it is necessary to subculture these organisms on agar plates in order to obtain pure cultures. It is these isolated colonies that are subjected to identification testing by the present invention. A detailed discussion of specimen collection and preparation is described in the *American Society of Microbiology Manual of Clinical Microbiology*, 2nd Ed. Lennette, E. H., Spaulding, E. H., and Truant, J. P., Editors, ASM, Washington, D.C. 1974.

In time sequence, once a culture is obtained, brought to the laboratory, and plated on agar plates for isolation, it is usually necessary to wait twelve to eighteen hours for there to be sufficient colonial growth for further testing. Once pure colonies have been isolated, the medical technologist makes a preliminary identification based on the colonial morphology and the microscopic appearance of the bacteria. To assist in this classification, the bacteria are stained with a dye and iodine mordant together with a red counterstain. If the bacterial walls have affinity for the stain, they will appear blue and are referred to as "Gram Positive". If the bacteria do not stain positively, the red counterstain will prevail; and these organisms are classified as being "Gram Negative". A well-isolated colony is transferred into eight ml. sterile saline which is supplemented with 0.02% Tween 80.

The saline suspension of bacteria is transferred into a plastic seed tray, and a transfer lid is placed over the tray. The transfer lid contains plastic prongs that are spaced in such a way that each prong will pick up a small but uniform drop of bacteria suspension and mate with the wells 33 in another plastic tray 14 that contain biochemical reagents. After the bacteria have been introduced to the biochemical microtubes 33, certain tubes (H S, lysine, arginine, and ornithine) are overlayed with mineral oil to seal the reaction mixtures from atmospheric oxygen. The biochemicals containing bacteria are incubated in a non-CO incubator at 35° C. for 18-24 hours. The reactions may then be read by the instrument 10, presently described.

The biochemical tests which are read and interpreted by this invention span a wide range of fermentative reactions. The following list expands in detail these biochemical reactions.

Carbohydrate Fermentation

The carbohydrates used with this invention are dextrose, sucrose, raffinose, rhamnose, arabinose, inositol, adonitol, and cellobiose. The fermentation of a specific carbohydrate results in acid formation. The resulting drop in pH is detected by a phenol red indicator changing the color from red to yellow.

Urea

Bacteria which produce urease split urea forming two molecules of ammonia. Since ammonia is basic, the resulting rise in pH can be detected by a phenol red pH indicator changing the color from orange to red.

Indole

The metabolism of the amino acid tryptophane results in the formation of indole which is detected by the addition of Kovac's reagent. If indole is present, a red color develops.

Lysine, Arginine, Ornithine

Decarboxylation of these compounds results in an alkalization of the media which is detected by the pH indicator bromcresol purple. A positive reaction is brown and a negative reaction is colorless to gray.

Tryptophane Deaminase

Bacteria capable of deaminating tryptophane produce phenyl pyruvic acid. In the presence of ferric ammonium citrate, this reaction product produces a brown color, whereas a negative reaction is clear.

Esculin Hydrolysis

The ability of an organism to hydrolyze esculin is detected by ferric ammonium citrate in the medium, which reacts with the hydrolysis products to form a black precipitate.

Voges Proskauer

Acetoin is produced from sodium pyruvate and indicated by the formation of a red color after addition of KOH and alpha-naphthol.

O.N.P.G.

Beta galactosidase hydrolizes orthonitrophenylbetagalactose, which liberates the yellow colored orthonitrophenyl.

Citrate, Malonate, Acetamide, Tartrate

The utilization of these substrates as the sole source of carbon for metabolism results in a rise in pH that is detected as a shift of green to blue by the pH indicator bromthymol blue.

O. F. Carbohydrates

Oxidation or fermentation of a carbohydrate results in acid formation. The consequent drop in pH is detected as a shift from blue or dark green to yellow or light green by the pH indicator bromthymol blue.

Nitrate

The ability of an organism to reduce nitrate to nitrite is detected by the addition of alpha-naphthylamine and sulfanilic acid, which produce a red color in the presence of nitrite. To confirm that nitrate has not been reduced to nitrogen gas, zinc powder is added to all negative tests to detect the presence of unreduced nitrate. This test is performed before the plate is read by the instrument, and the results are manually entered when the instrument's display queries the operator.

Starch Hydrolysis

Starch reacts with Gram's iodine to produce a blue-black color. If an organism hydrolyzes starch, the absence of starch is detected by the iodine yielding a brown rather than blue-black color.

Oxidase

Like nitrate, this test is performed "off-line" and manually entered into the instrument on command. The recommended oxidase test is the tetramethyl-p-phenylenediaminedihydro-chloride procedure described on page 679 of the second edition of the ASM Manual of Clinical Microbiology cited above.

MacConkey

MacConkey's agar is a selective medium that is used to differentiate major groups of gram negative microorganisms from one another. Growth or no-growth on this medium is manually entered into the instrument on command.

The organisms presently identified by this system are gram negative bacilli. These fall into two major classifications: enteric, or dextrose fermentors; and non-enteric, or dextrose non-fermentors. The following list includes a number of organisms that are identified by the present system:

| DEXTROSE FERMENTERS | DEXTROSE NON-FERMENTERS |
|---|---|
| Escherichia coli | Pseudomonas aeruginosa |
| E. coli indole neg. | Ps. fluorescens |
| E. coli H2S pos. | Ps. putida |
| E. coli urea pos. | Ps. cepacia |
| E. coli adecarboxylata | Ps. maltophilia |
| Shigella dysenteriae | Ps. stutzeri |
| Sh. flexneri | Ps. putrefaciens |
| Sh. boydii | Ps. pickettii |
| Sh. sonnei | Flavobacterium meningosept. |
| Edwardsiella tarda | Flavo. species |
| Salmonella enteriditis | Acinetobacter anitratus |
| Sal. typhi | Ac. lwoffi |
| Sal. cholera-suis | Achromobacter sp. |
| Sal. paratyphi A | A. xylosoxidans |
| Arizona hinshawii | Moraxella |
| Citrobacter freundii | B. bronchiseptica |
| Ci. diversus | Alkaligenes sp. |
| Ci. amalonaticus | Eikenella corrodens |
| Klebsiella pneumoniae | CDC Group II F |
| Kl. oxytoca | CDC Group II J |
| Kl. ozaenae | CDC Group II K-1 |
| Kl. rhinoscleromatis | CDC Group II K-2 |
| Enterobacter aerogenes | CDC Group IV C-2 |
| Ent. cloacae | CDC Group VE-1 |
| Ent. agglomerans | CDC Group VE-2 |
| Ent. gergoviae | |
| Ent. sakazakii | |
| Hafniae alviae | |
| Serratia marcescens | |
| Ser. liquefaciens | |
| Ser. rubidea | |
| Proteus vulgaris | |
| Prot. mirabilis | |
| Morganella morganii | |
| Providencia rettgeri | |
| Prov. stuartii | |
| Prov. alcalifaciens | |
| Yersinia enterocolitica | |
| Y. pestis | |
| Y. pseudotuberculosis | |
| Chromobacter violacium | |
| Pasteurella sp. | |
| Past. multocida | |
| Aeromonas hydrophilia | |
| Vibrio cholera | |
| Vibrio parahemolyticus | |

| DEXTROSE FERMENTERS | DEXTROSE NON-FERMENTERS |
|---|---|
| *V. alginolyticus* | |
| *Plesiomonas shigelloides* | |

The data base in the present invention thus may be the frequency of occurrence of twenty-one chemical reactions with seventy-seven different organisms, or a total combination of 1,617 probabilities.

The following three cases will be considered: (1) A *Pseudomonas aeruginosa* infection of the kidneys of a patient with chronic pyelonephritis, (2) A case of *Klebsiella pneumoniae* infection of the lungs in an alcoholic, (3) A case of *Salmonella enteritis* in a patient who owns a pet turtle.

The first patient was a middle aged woman who has had chronic urinary tract infections with flank pain and fever for many years. She was sent to a laboratory where a urine specimen was passed for bacterial analysis. The urine was streaked onto an agar plate with a calibrated platinum loop so that a quantitative estimate of bacteria growth could be obtained. A growth of similar appearing colonies were obtained that numbered over 100,000 per milliliter. The organism grew on McConkey's agar, and was both nitrate and oxidase positive. Several similar colonies were suspended in saline (salt solution) for evaluation by the instrument being described.

The second patient was an alcoholic who was found unconscious and brought to a county hospital. He subsequently suffered pneumonia, and a sputum specimen was obtained for bacterial evaluation. When the sputum cup was sent to the laboratory, representative portions were streaked onto various types of agar plates, and the next day, colonies were noted that to the technologist did not appear to be normal flora. A gram stain of these organisms revealed gram negative bacilli, so the technologist made the decision for further evaluation. A suspension of the bacteria was made in saline for further testing.

The third case was that of a grade school pupil who had a sudden onset of diarrhea. Upon questioning, the physician learned that the child had recently been given a pet turtle. The mother was asked to send the child and turtle to a local laboratory so they could obtain stool specimen from both the child and the turtle. The technologist plated representative parts of the stool on several types of selective agar, and there were some suspicious colonies that warranted further evaluation. These colonies were placed into saline for further identification by the present invention.

All of the three specimens had bacteria isolated from them that contained bacteria suspicious for disease. These bacterial colonies were placed into a saline suspension and thoroughly agitated to obtain optimum dispersion. The saline suspension was poured into a sterile plastic dish, and a transfer lid containing a matrix of 96 prongs was used to inoculate a drop of bacterial suspension into each of 96 wells of a plastic tray. The wells contained antimicrobic dilutions as well as biochemical substrates and indicators. The trays were allowed to incubate overnight; and the next day, following proper calibration, were placed into the instrument for automatic identification. The instrument made a reading of each of the wells through appropriate filters, and a table residing in computer memory interpreted these digitized voltages as either a positive reaction or a negative reaction. The computer then went through each of the seventy-seven possible organisms and computed the probability of occurrence. With the three present organisms, the frequencies and results obtained by the instrument are summarized in the following table:

| BIOCHEMICAL | PS. AERUGINOSA FREQ. | RESULT | K. PNEUMONIAE FREQ. | RESULT | S. ENTERITIDIS FREQ. | RESULT |
|---|---|---|---|---|---|---|
| Dextrose | 0.01 | neg | 99.9 | pos | 99.9 | pos |
| Sucrose | — | | 99.0 | pos | 00.6 | neg |
| Sorbitol | — | | 99.4 | pos | 95.0 | pos |
| Raffinose | — | | 99.2 | pos | 3.0 | neg |
| Rhamnose | — | | 99.3 | pos | 90.0 | pos |
| Arabinose | — | | 99.9 | pos | 99.9 | pos |
| Inositol | — | | 98.0 | pos | 30.0 | pos |
| Adonitol | — | | 90.0 | pos | 00.1 | neg |
| Cellobiose | — | | 99.0 | pos | 5.0 | neg |
| Urea | 50.0 | pos | 90.0 | pos | 00.1 | neg |
| H2S | 00.1 | neg | 00.1 | neg | 95.0 | pos |
| Indol | 00.1 | neg | 6.0 | neg | 1.0 | neg |
| Lysine | 00.1 | neg | 98.0 | pos | 95.0 | pos |
| Arginine | 95.0 | pos | 1.0 | neg | 50.0 | pos |
| Ornithine | 00.1 | neg | 1.0 | neg | 97.0 | pos |
| Tryptophane | 00.1 | neg | 00.1 | neg | 00.1 | neg |
| Esculin | 00.1 | neg | 99.0 | pos | 1.0 | neg |
| V.P. | 00.1 | neg | 90.0 | pos | 00.1 | neg |
| O.N.P.G. | 00.1 | neg | 99.0 | pos | 1.0 | neg |
| Citrate | 95.0 | pos | 98.0 | pos | 90.0 | pos |
| Malonate | 90.0 | pos | 94.0 | pos | 00.6 | neg |
| OF Glucose | 95.0 | pos | — | | — | |
| OF Maltose | 00.1 | neg | — | | — | |
| OF Xylose | 85.0 | pos | — | | — | |
| Acetamide | 90.0 | pos | — | | — | |
| Tartrate | 00.1 | neg | — | | — | |
| Starch | 00.1 | neg | — | | — | |
| Nitrate | 75.0 | pos | — | | — | |
| MacConkey | 85.0 | pos | — | | — | |
| Oxidase | 99.9 | pos | — | | — | |

The table of probabilities stated above are relevant only to positive reactions. If, in fact, the reactions were negative, the result would be 1.0 minus this probability. For instance, with the sucrose reaction of *S.enteritidis*, the probability for a positive reaction would be 00.6%, but since the reaction was negative, the actual probability is 99.4%.

Each of the actual probabilities of each biochemical reaction are cumulatively multiplied for each of the seventy-seven organisms in the data base to obtain the net probability for each organism. The organism with the highest net probability is the most likely organism. If the net probability of the most likely organism is less than $1 \times 10^{-6}$, then the instrument flashes a warning to the operator that the frequency is low, and possible technical errors should be checked out. If the net probability is greater than this value, then the instrument proceeds to normalize. This is done by dividing each of the organisms' net probabilities by the sum of all of the net probabilities. Thus, an estimate of the probabilities relative to each of the organisms is obtained. In the case of the three examples described above, these normalized probabilities are greater than 95%, so the instrument proceeds to display the most likely organism's probability on a thirty-two character Burroughs display and print the most probable organism's genus and species on a Practical Automation Model DMTP-9 alpha-numeric ticket printer.

A specific example of procedure (FIGS. 15A, 15B, and 15C)

The flow sheets 15A, 15B, and 15C illustrate procedure according to the present invention, after the type of tray-checking etc. shown in FIGS. 7A, 7B, and 7C.

Thus, when the device is instructed to commence, at start 300, the apparatus determines at 301 whether there is a tray 14 containing biochemicals in place or not. If there is no such tray 14 the light transmission will be the same for all wells and such a known transmission will give the answer "No"; then the computer returns at 302 to the main program. If the light transmissions result in the answer "Yes", then the dextrose voltage is read at 303 and the value compared at 304 with the stored positive-negative table in the computer. If the answer is positive, the organism is a dextrose fermenter and each of the biochemicals in receptacles 1 through 21 are read in at 305.

If the answer is "No", the organism is a dextrose non-fermenter, and the next stage is for the operator to enter manually whether the organism grew or did not grow on MacConkey's agar, at 306. This is an "off-line" test. If it grew, the operator enters "1"; if not, he enters "0". The processor waits for this input and stores the data at 307. Next, the operator manually enters "1" if oxidase is present or "0" if it is not present, as determined by another "off-line" test, queried and entered at 308; the processor again waits for the data and stores it at 309. A third "off-line" test used when the organism is not a dextrose fermenter is the nitrate test, and the operator is queried and enters the nitrate at 310 as either "1" or "0", depending on whether it is present or not, and at 311 the processor again waits for the data and stores it. After that, the biochemicals receptacles 10–27 are read in at step 312.

Thus, if the dextrose test is positive, the results for biochemicals 1 to 21 are read into the program at 305; if the dextrose results are negative, the presence or absence of MacConkey's growth, oxidase, and nitrate are determined and then the results for biochemicals 10 to 27 are read in.

In either event, the next step (after either 305 or 312, whichever is applicable) is the step 313, where the stored data in the tables is used to determine for each biochemical still pertinent (1 to 21 or 10 to 27) whether each is positive or negative. Step 314 then stores the positive and negative indications in a table or as packed data, in terms of probabilities. If any reaction is negative, then the probability used is 1.000 minus the actual negative probability, as box 315 shows. E.g., a negative probability of 99.5% is stored as 0.005. As this point, in box 316, the biotype is calculated and stored.

The next step 317 (FIG. 15B) multiplies the probabilities of each taxon and accumulates the sum, and then at step 318 sets up a table of non-normalized probabilities for each taxon. From this, the computer then sorts at 319 the three organisms with the highest probabilities.

If at step 320 the most frequent probability found is less than $1 \times 10^{-6}$, step 321 displays to the operator "VERY RARE BIOTYPE" and instructs the operator to call the company that provides the trays, and then the device returns at 322 to the main program for this answer is unacceptable. If the answer if "No" then the comparator determines at step 323 whether the most frequent organism is greater than $1 \times 10^{-6}$ but less or equal to $1 \times 10^{-5}$. If the answer is "Yes" the display at 324 says "RARE BIOTYPE-PRINT? (1 or 0)". If the operator wishes to go ahead and print this information he presses "1" on the keyboard, steps 325 and 326. If he presses "0", the computer returns to the main program at 327.

If he presses "1", or if the most probable organism has a probability greater than $1 \times 10^{-5}$, then the computer normalizes the three most probable organisms at step 328, by dividing the three highest frequencies by the sum of all the frequencies.

In FIG. 15C, the output from step 328 is dealt with. If the most probable organism has a normalized frequency between 0.950 and 0.999 (as asked at step 329), then the machine prints that one (or ones) out at step 329 in terms of probability percentage (e.g., 98.21%) and returns to the dextrose positive flag at 331.

If the most probable organism has a normalized frequency between 0.850 and 0.950 (step 332), that organism and its percentage are printed out at step 333, and the program goes to step 331 to determine again whether the organism is a dextrose fermenter or not.

If the response to both steps 329 and 332 is negative and if the most probable organism has a probability between 0.75–0.85 at step 334, then it is printed out at the step 335 and the percentage indicated, and the program at that point goes to step 331 for dextrose determination. If the relative probability of the most probable organism is less than 75%, the display first says "LOW SELECTIVITY RECHECK" at step 336, followed one second later by "0000000000000—XX.X%" at step 337, followed in turn one more second later by "STILL WANT TO PRINT? (1 OR 0)" at step 338. If at step 339 the operator does want to print, he presses "1" at step 240 and the information is printed, followed by sending the program to step 331 for the question of whether the dextrose is positive or negative. If the answer is "no", he presses "0" and returns to the main program at 341.

The step 342 asks whether the dextrose is positive, and if the answer is "yes", then the program goes via an output line 342. If the answer is "no" then the organism is evaluated for its sensitivity to the antibody Colistin. Comparison of Colistin with expected result for the organism is made at step 343 and then at step 344. The program looks up a table to see whether the result is correct. If not, it displays "RECHECK ID & COLISTIN DISAGREE" and goes to the output line 342. If the answer is "Yes", a similar procedure is performed at steps 346, 347, and 348 with the antibiotic Nitrofurantoin.

A "Yes" result leads to step 349 where the most probable organism and biotype number are printed. The output from dextrose positive along line 342 and from the two recheck steps 345 and 348, also go to this step 349. After that has been printed, the computer returns to the main program at 350.

TABLE OF PROGRAM FOR ANTIBIOTIC SUSCEPTIBILITY TESTING

The following listing constitutes the program for antibiotic susceptibility testing in hexadecimal code for direct loading into the programmable read only memory 142 of a type 6800 singal chip microprocessing unit, as made by Motorola American Microprosystems, and others.

Address                                    Program Instructions

```
0100 CE 30 00 6F 05 6F 04 86 2C A7 05 6F 07 86 7F A7
0110 06 C6 04 E7 07 6F 09 86 0F A7 03 86 0D A7 09 86
0120 2D A7 0B 6F 0D 86 F0 A7 0C 86 0D A7 0D 6F 0F 86
0130 FF A7 0E C6 2C E7 0F 7F 87 E8 7F 87 E9 C1 C1 01
0140 7E F1 3E C1 C1 01 01 C1 01 01 01 01 01 01 01 01
0150 01 01 01 C1 01 C1 7F 87 D1 7F 87 E0 7F 87 E1 4F
0160 8D 3D 43 84 F0 26 06 CE F5 74 43 20 0C 86 4F 8D
0170 2E 43 84 F0 27 07 CE F5 61 B7 87 D1 39 86 47 8D
0180 1E 43 84 F0 27 08 CE F6 10 B7 87 E0 20 07 CE F6
0190 1F 43 B7 87 E1 BD F3 36 BD F2 F5 BD F2 CF 39 B7
01A0 80 06 C6 60 ED F2 B9 B6 80 04 BD F2 F5 B6 80 C4
01B0 39 01 01 C1 BD F0 56 36 87 D1 26 6C CE F5 D4 BD
01C0 F2 4A 20 03 BD F2 50 B6 87 D5 27 03 7E F2 98 B6
01D0 87 D6 27 F0 BD F3 36 BD F2 F5 CE F6 2E BD F2 CF
01E0 86 0A BD F2 BD CE 84 00 B6 87 E0 26 03 CE 84 A0
01F0 B6 87 D5 27 03 7E F2 98 BD F3 60 B6 87 D5 27 15

0200 B6 87 E0 27 03 7F 87 E8 B6 87 E1 27 03 7F 87 E9
0210 7E F2 98 01 01 B6 87 E0 27 03 B7 87 E8 B6 87 E1
0220 27 03 B7 87 E9 CE F5 8E BD F2 47 B6 87 D5 27 F3
0230 CE F5 9B BD F2 47 B6 87 D4 27 F8 CE F5 29 BD F2
0240 47 B6 87 D6 27 03 7E F0 E1 B6 87 D7 26 03 7E F1
0250 3B 01 01 01 BD F0 43 B6 87 D1 27 03 7E F1 28 B6
0260 87 E0 27 0B B6 87 E8 26 10 CE F5 4B 7E F1 23 B6
0270 87 E1 27 F5 B6 87 E9 27 F0 86 03 BD F2 BD CE F5
0280 A9 BD F2 47 B6 87 D5 27 03 7E F2 98 B6 87 D8 27
0290 F0 CE F5 C9 BD F2 47 B6 87 D5 27 03 7E F2 98 B6
02A0 87 D7 27 F0 86 FF B7 87 A0 B7 87 A3 B7 87 A4 BD
02B0 F2 FA BD F3 47 7E F6 FE 01 01 01 01 01 01 01 01
02C0 01 01 01 01 01 01 01 01 01 01 01 01 01 01 01 01
02D0 01 01 01 01 01 01 01 01 01 01 01 01 01 01 01 01
02E0 01 01 01 01 01 01 01 01 01 01 01 01 01 01 01 01
02F0 01 01 01 01 01 01 01 01 01 01 01 01 01 01 01 01

0300 CE 87 A4 B6 80 08 85 20 26 F9 B6 80 08 85 10 27
0310 F9 C6 08 64 00 25 04 86 0E 20 02 86 0F B7 80 08
0320 B6 80 0A B7 80 0A 4F 4C 26 FD 5A 26 E6 09 3C 87
0330 9F 27 09 8C 87 A0 26 D9 C6 04 20 D7 86 02 B7 80
0340 08 86 0E B7 80 08 39 BD F3 36 BD F2 F5 BD F2 CF
0350 FF 87 D2 CE 87 D4 6F 00 08 8C 87 D9 26 F3 FE 87
```

| Address | Program Instructions |
|---|---|

```
0360 D2 0E 3E 39 CE 30 00 A6 0D 35 30 27 03 B7 87 D4
0370 85 40 27 03 B7 37 D5 E6 0C A6 09 85 80 27 03 B7
0380 37 D6 85 40 27 03 B7 37 D7 E6 08 A6 0B 85 80 27
0390 03 B7 87 D8 E6 0A 0E 3B 36 04 CE F5 37 36 7F 80
03A0 0E C6 80 BD F2 B9 BD F3 36 BD F2 CF C6 30 BD F2
03B0 B9 32 4A 26 E5 7E F1 25 5F 86 01 20 01 5F 37 5F
03C0 5A 01 01 01 01 26 F9 33 5A 26 F3 4A 26 F0 39 FF
03D0 87 D2 E6 00 27 0A 36 AA B7 30 0E 3D 18 5A 26 F6
03E0 E6 01 08 A6 01 84 3F 8B 80 B7 80 0E 8D 07 5A 26
03F0 F1 FE 87 D2 39 4F 4A 26 FD 39 BD F3 36 36 F7 CE 0400 87 A1 0D 49 25 0C BD F3 47 BD F2 00 BD F3 47 01
0410 01 39 B7 80 0C F6 80 0C C4 0F 37 43 85 50 26 07
0420 EB 00 E7 00 03 20 06 58 58 58 58 E7 00 33 43 CB
0430 80 F7 80 0E 20 CC C6 20 7F 80 0E BD F2 F5 86 AA
0440 B7 80 0E 5A 26 F5 39 B6 80 03 35 20 26 F9 B6 80
0450 03 85 10 27 F9 36 04 B7 80 03 36 0E B7 80 03 39
0460 7F 80 06 C6 60 BD F2 B9 BD F2 F5 B6 80 04 BD F2
0470 F5 B6 80 04 43 A7 00 08 7C 80 06 B6 80 06 34 01
0480 26 E6 B6 80 06 84 78 81 50 26 D8 39 FE 87 D2 01
0490 BD F3 47 09 FF 87 D2 A6 50 A0 00 2B 1E BD F3 C1
04A0 B6 87 D3 84 F8 27 0E 81 A0 27 0A B7 87 D3 20 DC
04B0 01 01 01 01 01 39 01 01 01 01 36 07 16 B4 87
04C0 D3 26 D2 F7 87 A0 01 01 20 D3 FF 87 EE 5F CE F6
04D0 AE B6 87 E0 26 05 C6 A0 CE F6 5E B6 87 EF 10 FF
04E0 37 EE BB 87 EF 24 03 7C 87 EE B7 87 EF FE 87 EE
04F0 A6 00 01 01 CE 0F FF 85 07 27 1F CE 4F FF 35 06

0500 27 18 CE 44 FF 85 05 27 11 CE 44 4F 35 04 27 0A
0510 CE 44 44 85 03 27 03 CE 88 33 FF 87 A3 84 F3 44
0520 44 CE F6 34 FF 87 EE BB 87 EF 24 03 7C 87 EE B7
0530 87 EF FE 87 EE EE 00 FF 87 A1 B6 87 A0 26 03 7A
0540 87 A0 BD F2 00 39 01 01 01 01 01 01 01 01 01 01
0550 01 01 01 01 01 01 01 01 01 01 01 01 01 01 01 01
0560 01 01 01 01 01 01 01 01 01 01 01 01 01 01 01 01
0570 01 01 01 01 01 01 01 01 01 01 01 01 01 01 01 01
0580 01 01 01 01 01 01 01 01 01 01 01 01 01 01 01 01
0590 01 01 01 01 01 01 01 01 01 01 01 01 01 01 01 01
05A0 01 01 01 01 01 01 01 01 01 01 01 01 01 01 01 01
05B0 01 01 01 01 01 01 01 01 01 01 01 01 01 01 01 01
05C0 01 01 01 01 01 01 01 01 01 01 01 01 01 01 01 01
05D0 01 01 01 01 01 01 01 01 01 01 01 01 01 01 01 01
05E0 01 01 01 01 01 01 01 01 01 01 01 01 01 01 01 01
05F0 01 01 01 01 01 01 01 01 01 01 01 01 01 01 01 01

0600 08 10 49 4E 53 45 52 54 20 54 45 53 54 20 54 52
0610 41 59 05 15 49 4E 53 45 52 54 20 43 41 4C 49 42
0620 52 41 54 45 20 54 52 41 59 00 20 4E 45 58 54 20
0630 54 45 53 54 20 50 52 45 53 53 20 52 55 4E 20 4F
0640 52 20 43 41 4C 49 42 52 41 54 45 03 14 43 41 4C
0650 49 42 52 41 54 49 4F 4E 20 52 45 51 55 49 52 45
0660 44 07 11 55 4E 49 44 45 4E 54 49 46 49 45 44 20
0670 54 52 41 59 07 11 54 52 41 59 20 49 4E 20 42 41
0680 43 4B 57 41 52 44 53 0D 05 45 52 52 4F 52 0A 0B
0690 52 45 4D 4F 56 45 20 54 52 41 59 0A 0C 43 4C 4F
06A0 53 45 20 44 52 41 57 45 52 01 1E 53 45 54 20 50
06B0 41 54 49 45 4E 54 20 49 44 20 41 4E 44 20 49 4E
06C0 53 45 52 54 20 46 4F 52 4D 0B 09 50 52 45 53 53
```

| Address | Program Instructions |
|---|---|

```
06D0  20 52 55 4E 02 0F 50 52 45 53 53 20 43 41 4C 49
06E0  42 52 41 54 45 06 13 49 4E 53 55 46 46 49 43 49
06F0  45 4E 54 20 47 52 4F 57 54 48 06 14 53 54 45 52

0700  49 4C 45 20 43 4F 4E 54 41 4D 49 4E 41 54 45 44
0710  00 0D 47 52 41 4D 20 50 4F 53 20 54 52 41 59 00
0720  0D 47 52 41 4D 20 4E 45 47 20 54 52 41 59 0E 04
0730  57 41 49 54 51 2A 25 6A 12 3A 64 A0 32 A0 16 A0
0740  8A 00 4A 00 2A 00 1A 00 0A 50 0A 25 0A 12 0A 06
0750  60 8A 30 4A 15 2A 76 A0 33 A0 19 A0 9A 50 23 31
0760  3A 43 4C 54 5C 05 18 21 29 32 3B 44 4C 05 2D 31
0770  3A 42 4B 54 5C 05 28 30 3A 43 4B 54 5C 05 C0 09
0780  11 19 22 2A 1B 05 20 29 32 3B 43 4C 54 05 1D 20
0790  29 32 3B 43 4C 05 28 30 39 42 4B 53 5C 05 CC 08
07A0  10 1B 23 2B 33 C5 70 73 81 3A 93 9C A4 05 28 30
07B0  39 42 4B 54 5C 05 28 31 39 42 4B 54 5C 05 28 31
07C0  3A 43 4B 54 5C 05 39 42 4B 53 5C 64 6C C5 18 21
07D0  29 32 3B 44 4C 05 2D 31 3A 42 4B 54 5C 05 28 30
07E0  3A 43 4B 54 5C 05 0C 09 11 19 22 2A 33 05 0C 03
07F0  10 1B 23 2B 33 05 70 73 81 3A 93 96 A4 C5 CE 34

0800  50 E6 87 E0 26 03 CE 34 F0 FF 87 D2 BD F3 60 36
0810  87 D5 27 03 7E F2 98 CE 34 00 E6 37 E0 26 C3 CE
0820  84 A0 A6 07 A0 57 2A 01 40 81 CA 2F 06 CE F5 FA
0830  7E F1 28 A6 CF A0 5F 2A 01 40 CE F5 E5 81 0A 2D
0840  EF BD F3 8C 7E F1 25 01 01 01 01 01 01 01 01 01
0850  01 01 01 01 01 01 01 01 01 01 01 01 01 01 01 01
0860  01 01 01 01 01 01 01 01 01 01 01 01 01 01 01 01
0870  01 01 01 01 01 01 01 01 01 01 01 01 01 01 01 01
0880  01 01 01 01 01 01 01 01 01 01 01 01 01 01 01 01
0890  01 01 01 01 01 01 01 01 01 01 01 01 01 01 01 01
08A0  01 01 01 01 01 01 01 01 01 01 01 01 01 01 01 01
08B0  01 01 01 01 01 01 01 01 01 01 01 01 01 01 01 01
08C0  01 01 01 01 01 01 01 01 01 01 01 01 01 01 01 01
08D0  01 01 01 01 01 01 01 01 01 01 01 01 01 01 01 01
08E0  01 01 01 01 01 01 01 01 01 01 01 01 01 01 01 01
08F0  01 01 01 01 01 01 01 01 01 01 01 01 01 01 01 01
```

Concerning Comparisons

As indicated above, the apparatus of this invention is capable of performing various types of comparisons. Any specific comparison depends upon what method is being used and which types of comparison are appropriate.

In some instances, there may be only one comparison, the specific type of comparison depending on the particular apparatus or particular method being used. For example, it is advisable to relate for every sample the signal received from each well with a signal of a reference transducer. Such comparison negates the effect of the variation of light intensity or power fluctuation with time.

A second type of comparison is often made, in addition to the first one. This may be considered as a type of calibration procedure aimed at negating the variation of response of the different photosensors. The comparison may be achieved by storing the signals from each of the photosensors before the tray is introduced, and then subtracting from this the corresponding signals generated by each of the wells after the filled tray with its cultured samples has been read. This technique of eliminating transducer-to-transducer variation is important.

Further refinements, which are not necessarily crucial, may be added to eliminate further well-to-well variation. For example, variations in the plastic trays or their contents may affect the accuracy of a reading. One way to eliminate this problem is to calibrate with an empty tray instead of calibrating without any tray in the holder. A single empty tray may be used, assuming that all the trays to be used are substantially identical. Another approach is to compare the wells of each individual tray when empty with the results obtained after filling them with liquid and culturing the liquid. This is more time consuming and not usually necessary, but it is more accurate. With suitable multiplexing wired into the device, however, this becomes quite practical. Thus, it is possible to eliminate the variations in the signal fluctuating with time, to eliminate the variation of one sensor versus another, and also to compensate for tray-to-tray and well-to-well variations.

A third type of comparison may be used for certain tests, such as the MIC test, where the signal level indicating bacterial growth is differentiated from the signal level indicating no growth. This may be accomplished by comparison between various wells on the tray; that is, some wells may be control wells or sterile no-growth wells, in which there is no growth or which are inoculated with suitable inhibitors. There is a possible interpolation between the values of growth and no-growth, as discussed above. Alternatively, by experimentation, one can determine a signal value that differentiates between growth and no-growth, and this decision point may be used instead of one derived by controls on board each tray.

Some of the claims which follow specifically identify the types of comparisons made, while others merely call for suitable comparisons to be made or for apparatus which make these comparisons possible.

The above described preferred embodiments provide apparatus and a method for automatically determining the minimum inhibitory concentration of a plurality of different antibiotics necessary to stop growth of an infective organism being tested. Minimum inhibitory concentration information is also transferred to dosage information by the apparatus and method of the invention. The required time to perform such a test is greatly reduced in comparison to other methods, a great deal more information is provided, and accuracy is improved. Various other embodiments and variations to the preferred embodiments will be apparent to those skilled in the art and may be made without departing from the spirit and scope of the following claims.

We claim:

1. A method for performing simultaneously a plurality of interrelated optical density tests, employing a sample tray having a multiplicity of wells in rectangular grid arrangement containing liquid samples, said wells having translucent bottoms, comprising:

holding said tray accurately in a single predetermined stationary reading position without blocking off light paths through said wells, sending light from a light source through all said wells at approximately the same intensity to an array of light-intensity-detecting well-associated photocells, there being one photocell adjacent to each well, while simultaneously sending light directly from said light source to a reference detecting photocell without passing the light through a said sample, electronically sequentially transmitting the signals from all said photocells in a prescribed order, each signal corresponding to the intensity of light received by a said photocell, sequentially comparing the signal from each said well-associated photocell of said array with the simultaneous signal from said reference detecting photocell and developing a related signal therefrom for each well indicating a first adjusted value for each well, sequentially making an electronic comparison of each said related signal value with an electronically stored data reference value corresponding to a preliminary value for each well derived like said first adjusted value without interposing the sample between said light source and any of said well-associated photocells, and developing a resultant value from that comparison, sequentially comparing electronically said resultant values with one another for said interrelated optical density tests and with other stored values and determining a conclusion therefrom, and reading out the desired results thereby obained.

2. The method of claim 1 wherein the step of developing a related signal comprises generating a signal as a ratio of each signal derived via a well to the signal derived from the reference photocell.

3. The method of claim 2 wherein the step of developing a resultant value comprises generating another ratio signal as the ratio of said related signal to a similarly derived ratio signal obtained by initially reading the photocells unobstructed by the tray.

4. The method of claim 2 wherein the step of developing a resultant value comprises generating another ratio signal as the ratio of said related signal to a similarly derived ratio signal obtained by reading the tray wells filled with the liquid but before any growth or culture thereof.

5. A method for performing simultaneously a plurality of interrelated optical density tests, employing a sample tray having a multiplicity of wells in a rectangular grid, said wells having translucent bottoms, comprising:

(a) sending light from a light source vertically at approximately the same intensity to an array of light-intensity-detecting well-associated photocells, there being one photocell corresponding to each well, (b) while simultaneously sending light directly from said light source to a reference detecting photocell, (c) electronically sequentially transmitting the signal from all said photocells in a prescribed order, each signal corresponding to the intensity of light received by a said photocell, (d) sequentially comparing the signal from each said photocell of said array with the simultaneous signal from said reference detecting photocell and developing a first related signal therefrom for each well-associated photocell, (e) storing said first related signal in a digital computer forming an integral part of the system, (f) holding the tray having its wells filled with liquid samples, accurately in a single predetermined reading position without blocking off light paths through said wells, (g) sending light from said light source vertically through all said filled wells at roughly the same intensity to the same said array of light-intensity-detecting well-associated photocells, there being one photocell for each well, (h) while simultaneously sending light directly from said light source to said reference detecting photocell without passing the light through a said sample, (i) electronically sequentially transmitting the signals for filled wells from all said photocells in a prescribed order, each signal corresponding to the intensity of light received by a said photocell, (j) sequentially comparing electronically, in the digital computer, the signal for the filled wells from each said photocell of said array with the signal from said reference detecting photocell and developing a second related signal therefrom for each well, (k) sequentially making an electronic comparison of each said second related signal value with the corresponding stored first related signal value for the same well, and developing a resultant value from that comparison, (l) sequentially comparing electronically said resultant values with one another for said interrelated optical density tests and with other stored values and determining a desired result from that comparison, and reading out the desired results thereby obtained.

6. A method for determining susceptibility of a bacteria culture to various antimicrobic drugs and of determining the minimum inhibitory concentration of the bacteria culture to those drugs to which it is susceptible, utilizing a plurality of interrelated optical density tests, comprising:

providing a microtube tray having a rectangular grid array of many light-transmissive wells, and a series of photodetectors, including a photodetector associated with each said well and a reference photodetector not associated with a tray well, each photodetector being adapted to provide a signal corresponding to the sensed light intensity, initially calibrating the photodetectors by passing light from a source of generally uniform intensity to the photodetectors and electronically sequencing the photodetectors to read a signal from each photodetector, comparing in a onboard computer the values of the signals obtained for each well-associated photodetector sequentially with the value of the reference signal obtained simultaneously for the reference photodetector, and providing an initial calibration value for each well-associated photodetector which is a function of the well photodetector signal and the reference signal, and with the computer, storing and retaining the calibration value for each wel-associated photodetector, placing in the wells a plurality of different antimicrobic drugs, each drug being included in a series of wells in serially diluted known concentration of the bacteria, and placing the wells adjacent to the well-associated photodetectors, following a period for bacterial growth, passing light of generally uniform intensity simultaneously through each well and to the reference photodetector and reading the intensity of the transmitted light with the photodetectors by electronically sequencing the photodetectors to read an after-culture signal from each, comparing in the computer the value of each after-culture signal obtained from the well-associated photodetectors sequentially with the value of the after-culture signal obtained substantially simultaneously from the reference photodetector and providing an after-culture value for each well-associated photodetector which is a function of the after-culture well photodetector signal and the after-culture reference signal, comparing in the computer, for each well, the after-culture value with the initial calibration value and providing a comparison signal for each well which allows for variations in the intensity of the light directed from the source onto the different wells and for variations in the sensitivities of the photocells, automatically and sequentially comparing in the computer the comparison signal values with one another and with a limit comparison signal value which represents a cutoff between inhibition and growth, correlating in the computer the comparisons with stored data identifying the antimicrobic drug and concentration in each well, and obtaining therefrom an indication of which antimicrobic drugs inhibit growth of the bacteria, automatically selecting with the computer the minimum inhibitory concentration of each inhibitory drug by selecting the minimum concentration of each drug which produced a comparison signal value on the inhibition side of the limit comparison signal value, and automatically displaying in situ the minimum inhibitory concentration for each inhibitory drug, and, for each drug that does not inhibit growth, displaying that the bacteria is resistant to that drug.

7. The method of claim 6 wherein each of the first three comparing steps comprises calculating with the computer a value representing the ratio of the two involved values, so that, in effect, a value representing the ratio of the first two comparison ratios is obtained as said comparison signal for each well, whereby any variations in the light output of the light source over time are cancelled out through use of ratios with the reference photodetector signal values, and constancy of light intensity from the source is not critical over either time or location.

8. The method of claim 7 wherein the calculation of a value representing the ratio of the two involved ratios comprises calculating the logarithm of the ratio of the two involved values, so that the third comparison step, wherein after culture values are compared with initial calibration values, comprises calculating a difference in logarithms.

9. The method of claim 8 wherein the placing step includes providing a sterile control well with no bacteria culture and providing a growth control well with bacteria culture but no antimicrobic drug, and further includeing calculating in the computer said limit comparison signal value, including taking the difference between the after culture values of these two wells and calculating a threshold which is a preselected portion of such difference away from the sterile control well after culture value.

10. The method of claim 9 wherein said preselected portion is about 25%.

11. The method of claim 6 wherein the placing step includes providing a sterile control well with no bacterial culture and providing a growth control well with bacterial culture but no antimicrobic drug, and further includeing calculating in the computer said limit comparison signal value, including taking the difference between the after culture values of these two wells and calculating a threshold which is a preselected portion of such difference away from the sterile control well after culture value.

12. The method of claim 11 which further includes the step of comparing, prior to calculating the limit comparison signal value, the calculated difference between the after culture values for the sterile and growth control wells with a predetermined, stored value representing adequate growth-sterile difference for the test, and if the calculated difference is less than the predetermined, stored value, displaying that the calculated difference is inadequate, so that a check on the test is provided.

13. The method of claim 6 which further includes automatically comparing, in the computer, the minimum concentration information for each inhibitory drug with information relating to dosages required to achieve such minimum concentrations at the required body sites, and automatically indicating the dosage range required to control the bacteria for each inhibitory drug.

14. The method of claim 13 which further includes indicating if the required dosage range may be toxic to the patient.

15. A method of identifying microorganisms, comprising:

placing a series of different reagents in a large number of wells arranged in a rectangular grid in a light-transmissive sample tray held stationary throughout the method, establishing a known uniform concentration of a culture of the microorganism and placing the uniform concentration in equal volumes in the wells, following a predetermined period for bacterial growth, passing light from a light source in substantially equal intensity through all said wells and through a color filter and collimator, according to the opacity value for each well, initiating an automatic sequence while the tray is held stationary of (a) automatically sensing the intensity of the collimated light transmitted through each well by photodetector means adjacent to the wells and filter and opposite the light source, (b) automatically and electronically sequentially comparing, in a computer, the opacity values for each well with an opacity for light from the same source not passing through any well but passing through the filter, and generating a signal from such comparison, (c) automatically and sequentially comparing that signal with a value corresponding to inhibited reaction for each well, (d) automatically and sequentially comparing the opacity values from different tests to obtain probability values for various suspected organisms, (e) automatically and sequentially comparing these probability values with computer-stored information about the suspected organisms, and (f) automatically and sequentially printing the names of the most probable organism and the computer probability values for each.

16. Apparatus for determining susceptibility of a bacterial culture to various antimicrobic drugs and for determining the minimum inhibitory concentration of the bacteria culture to those drugs to which it is susceptible, utilizing a plurality of interrelated optical density tests, said apparatus having a sample microtube tray with a large number of light-transmissive wells arranged in a rectangular matrix for containing uniform samples of the bacterial culture and series of varied concentrations of a plurality of antimicrobic drugs, comprising:

tray holding means for supporting the sample tray in a single accurate predetermined stationary position throughout the tests, assuring proper transmission of light through said wells, light source means positioned in vertical relationship to the sample tray for sending light of generally uniform intensity generally vertically through all wells simultaneously, a stationary array of light intensity detecting well-associated photocells opposite said light source means, one adjacent to each well and positioned to receive light from the light source which is transmitted through the well and its contents, a reference light-intensity-detecting photocell for receiving light from said light source means without passing through a said sample, sequential signal receiving means connected to all the photocells for receiving sequentially a signal from each said well-associated photocell in a prescribed order, and simultaneously with each said signal a signal from said reference photocell, each signal corresponding in amplitude to the intensity of light received by a said photocell and thus to the turbidity of the contents of the well, electronic sequencing means for delivering the photocell signals to said signal receiving means in an automatic sequence, rapidly, one at a time, data storage and recall means forming part of said apparatus for storing and recalling values relating to bacterial growth, including temporary storage means and permanent storage means, first comparator means connected to said signal receiving means, for sequentially comparing the signal from each said photocell of said array, after a period for bacterial growths with the signal received simultaneously from said reference detecting photocell and developing a related signal from those two signals, second data recall and comparator means connected to said first comparator means and to said data storage means for sequentially making a comparison of each said related signal value with a sequentially recalled data reference value corresponding to a temporarily stored pre-test value taken prior to any bacterial growth for each said well-associated photocell, and developing a resultant value from that comparison and storing the resultant values temporarily, third data recall and comparator means connected to said second comparator means and to said data storage means for sequentially comparing said temporarily stored resultant values with one another and for making comparisons with values corresponding to inhibited bacterial growth, determination means connected to said third data recall and comparator means for determining from said comparisons and from comparisons with pertinent permanently stored data, which antimicrobic drugs inhibit growth of the bacteria and for determining and indicating for each inhibitory drug the minimum concentration of that drug which will inhibit such growth.

17. The apparatus of claim 16, further including means associated with said third data recall and comparator means for calculating said values corresponding to inhibited bacterial growth, including calculating a threshold inhibited growth value which is a preselected portion of the difference between the after growth resultant values from a growth control well with bacteria culture but no antimicrobic drug and a sterile control well with no bacteria culture.

* * * * *